US006420136B1

(12) United States Patent
Riabowol et al.

(10) Patent No.: US 6,420,136 B1
(45) Date of Patent: Jul. 16, 2002

(54) METHOD OF MODULATING P53 ACTIVITY

(75) Inventors: Karl T. Riabowol, Calgary (CA); Igor Garkavtsev, Cambridge, MA (US); Andrei Gudkov, Glencoe, IL (US)

(73) Assignees: University Technologies International, Inc., Calgary (CA); Board of Trustees of the University of Illinois, Chicago, IL (US)

(*) Notice: Subject to any disclaimer, the term of this patent is extended or adjusted under 35 U.S.C. 154(b) by 0 days.

(21) Appl. No.: 09/159,871

(22) Filed: Sep. 24, 1998

Related U.S. Application Data

(63) Continuation of application No. 09/006,783, filed on Jan. 14, 1998, now Pat. No. 6,297,366.
(60) Provisional application No. 60/060,138, filed on Sep. 26, 1997.

(51) Int. Cl.[7] ............................ C12P 21/06; C12P 21/04; A01N 63/00; A01N 65/00; A01N 43/04
(52) U.S. Cl. ..................... 435/69.1; 424/93.1; 435/70.1; 435/320.1; 435/325; 514/44; 536/23.1; 536/23.5; 536/24.5; 530/350
(58) Field of Search .......................... 530/350; 536/23.1, 536/24.5, 23.5; 514/44; 424/93.1; 435/320.1, 325, 69.1, 70.1

(56) References Cited

U.S. PATENT DOCUMENTS 5,986,078 A * 11/1999 Garkavtsev et al. ........ 536/23.1
6,143,522 A * 11/2000 Helbing et al. ............. 435/69.1
6,238,918 B1 * 5/2001 Garkavtsev et al. ........ 435/325

FOREIGN PATENT DOCUMENTS

WO    WO97/21809    6/1997

OTHER PUBLICATIONS

Jones et al., Advanced Drug Therapy Reviews, vol. 31, pp. 153–170, 1998.*
Ross et al., Human Gene Therapy, vol. 7, Sep. 10, 1996, pp. 1781–1790.*
Anderson, Nature, vol. 392, Apr. 30, 1998.*
Verma et al., Nature, vol. 389, Sep. 1997.*
Atadja, et al., *Mol. Cell Biol.*, 14:4991–4999 (1994).
Atadja, P., et al., "Increased activity of p53 in senescing fibroblasts", *Proc. Natl'l. Acad. Sci. USA*, 92:8348–8352 (1995).
Chang, et al., "Gene Therapy: Applications to the Treatment of Gastrointestinal and Liver Diseases", *Gastroent.*, 106:1076–1084 (1994).
Garkavtsev, et al., "Suppression of the novel growth inhibitor p33$^{ING1}$ promotes neoplastic transformation", *Nature*, 14:415–420 (1996).
Garkavtsev, et al., "Cellular localization and chromosome mapping of a novel candidate tumor suppressor gene", *Cytogenetics and Cell Genetics*, 76:176–178 (1997).
Garkavtsev, et al., "Extension of the replicative life span of huma diploid fibroblasts by inhibition of the p33$^{ING1}$ candidate tumor suppressor", *Molecular and cellular Biology*, 17:2014–2019 (1997).
Herman, et al., "Methylation specific PCR: a novel PCR assay for methylation status of CpG islands", *Proc. Natl. Acad. Sci. USA*, 93:9821–9826 (1996).

(List continued on next page.)

Primary Examiner—Sheela Huff
Assistant Examiner—Jennifer Hunt
(74) Attorney, Agent, or Firm—Burns, Doane, Swecker & Mathis, L.L.P.

(57) ABSTRACT

This invention relates to a method for modulating the activity of the protein p53 in cells by the addition of a peptide or protein having p33$^{ING1}$ biological activity or a nucleic acid coding for such a peptide or protein.

2 Claims, 5 Drawing Sheets

OTHER PUBLICATIONS

Kane, et al., "Methylation of the hMLH1 promoter correlates with lack of expression of hMLH1 in sporadic colon tumors and mismatch repair–defective", *Cancer Res.*, 37:808–811 (1997).

Levine, A.J., "The Tumor Suppressor Genes", *Annu. Rev. Biochem.*, 62:623–651 (1993).

Levine, A.J., "p53, the cellular gatekeeper for growth and division", *Cell*, 88:323–331 (1997).

Shulman, et al., "A better cell line for making hybridomes secreting specific antibodies", *Nature*, 276:269–270, (1978).

Wong, H., et al., "Monitoring mRNA expression by polymerase chain reaction: the "primer–dropping" method", *Anal. Biochem.*, 223:251–258 (1994).

Yang, Y., et al., "An approach for treating the hepatobiliary disease of cystic fibrosis by somatic gene transfer", *Proc. Nat'l. Acad. Sci. USA*, 90:4601–4605 (1993).

* cited by examiner

FIGURE 1

```
                                                           GAG TAA CCC GAT AAT
  16 ATG CCG TTG TGC ACG GCG ACG AGA ATT CCC AGA TAT AGC AGT AGC AGT GAT CCC GGG CCT
   1 met pro leu cys thr ala thr arg ile pro arg tyr ser ser ser ser asp pro gly pro 76 GTG GCT CGG GGC CGG GGC TGC AGT TCG GAC CGC CTC CCG CGA CCC GCG GGG CCG GCT CGG
  21 val ala arg gly arg gly cys ser ser asp arg leu pro arg pro ala gly pro ala arg 136 AGA CAG TTT CAG GCC GCA TCT TTG CTG ACC CGA GGG TGG GGC CGC GCG TGG CCG TGG AAA
  41 arg gln phe gln ala ala ser leu leu thr arg gly trp gly arg ala trp pro trp lys 196 CAG ATC CTG AAG GAG CTA GAC GAG TGC TAC GAG CGC TTC AGT CGC GAG ACA GAC GGG GCG
  61 gln ile leu lys glu leu asp glu cys tyr glu arg phe ser arg glu thr asp gly ala 256 CAG AAG CGG CGG ATG CTG CAC TGT GTG CAG CGC GCG CTG ATC CGC AGC CAG GAG CTG GGC
  81 gln lys arg arg met leu his cys val gln arg ala leu ile arg ser gln glu leu gly 316 GAC GAG AAG ATC CAG ATC GTG AGC CAG ATG GTG GAG CTG GTG GAG AAC CGC ACG CGG CAG
 101 asp glu lys ile gln ile val ser gln met val glu leu val glu asn arg thr arg gln 376 GTG GAC AGC CAC GTG GAG CTG TTC GAG GCG CAG CAG GAG CTG GGC GAC ACA GTG GGC AAC
 121 val asp ser his val glu leu phe glu ala gln gln glu leu gly asp thr val gly asn
                                                                        1
 436 AGC GGC AAG GTT GGC GCG GAC AGG CCC AAT GGC GAT GCG GTA GCG CAG TCT GAC AAG CCC
 141 ser gly lys val gly ala asp arg pro asn gly asp ala val ala gln ser asp lys pro 496 AAC AGC AAG CGC TCA CGG CGG CAG CGC AAC AAC GAG AAC CGT GAG AAC GCG TCC AGC AAC
 161 asn ser lys arg ser arg arg gln arg asn asn glu asn arg glu asn ala ser ser asn 556 CAC GAC CAC GAC GAC GGC GCC TCG GGC ACA CCC AAG GAG AAG AAG GCC AAG ACC TCC AAG
 181 his asp his asp asp gly ala ser gly thr pro lys glu lys lys ala lys thr ser lys 616 AAG AAG AAG CGC TCC AAG GCC AAG GCG GAG CGA GAG GCG TCC CCT GCC GAC CTC CCC ATC
 201 lys lys lys arg ser lys ala lys ala glu arg glu ala ser pro ala asp leu pro ile 676 GAC CCC AAC GAA CCC ACG TAC TGT CTG TGC AAC CAG GTC TCC TAT GGG GAG ATG ATC GGC
 221 asp pro asn glu pro thr tyr cys leu cys asn gln val ser tyr gly glu met ile gly
                                                         2
 736 TGC GAC AAC GAC GAG TGC CCC ATC GAG TGG TTC CAC TTC TCG TGC GTG GGG CTC AAT CAT
 241 cys asp asn asp glu cys pro ile glu trp phe his phe ser cys val gly leu asn his 796 AAA CCC AAG GGC AAG TGG TAC TGT CCC AAG TGC CGG GGG GAG AAC GAG AAG ACC ATG GAC
 261 lys pro lys gly lys trp tyr cys pro lys cys arg gly glu asn glu lys thr met asp
                  3                      4
 856 AAA GCC CTG GAG AAA TCC AAA AAA GAG AGG GCT TAC AAC AGG TAG TTT GTG GAC AGG CGC
 281 lys ala leu glu lys ser lys lys glu arg ala tyr asn arg ***

916 CTG GTG TGA GGA GGA CAA AAT AAA CCG TGT ATT TAT TAC ATT GCT GCC TTT GTT GAG GTG
 976 CAA GGA GTG TAA AAT GTA TAT TTT TAA AGA ATG TTA GAA AAG GAA CCA TTC CTT TCA TAG
1036 GGA TGG CAG TGA TTC TGT TTG CCT TTT GTT TTC ATT GGT ACA CGT GTA ACA AGA AAG TGG
1096 TCT GTG GAT CAG CAT TTT AGA AAC TAC AAA TAT AGG TTT GAT TCA ACA CTT AAG TCT CAG
1156 ACT GAT TTC TTG CGG GAG GAG GGG GAC TAA ACT CAC CCT AAC ACA TTA AAT GTG GAA GGA
1216 AAA TAT TTC ATT AGC TTT TTT ATT TTA ATA CAA GTA ATA TTA TTA CTT TAT GAA CAA TTT
1276 TTT TTA ATT GGC CAT GTC GCC AAA AAT ACA GCC TAT AGT AAA TGT GTT TCT TGC TGC CAT
1336 GAT GTA TAT CCA TAT AAC AAT TCA GTA ACA AAG GTT TAA AGT TTG AAG ATT ATT TTT TAA
1396 AAA GGT AAA AGG TTA AAT TTT ACA TGA CAG ATA TTT TAT CTA TTG GCC TGT TCC CCA AAT
1456 GGC CAT TTT AAA ATG CTT GGG TAC ACT TCT CTT AAG TGG TCT AGT CAA GGA ACC TCA AGT
1516 CAT GCT TTT GCT ATC ACC AAT CAT AGT GTA CCC ATC TTT AAT TTA TAT CAG GTG TAT AAA
1576 TGT ACA TTT CCA AAT GAA CTT GCA CTG TAA TAT TAT AAT TGG AAG TGC AGT CAG CAG TAG
1636 CTG TCG GAG CTA ATG TCA CAA TTA TGT GCA AAG GTG TGC TTC CTG CTG TAT GTG AGC TGT
1696 AAA AAT GTT ACG TGA AGA AAT AAA TGA AAC TTG GCC AGT TTG TTC CTC TAG TAG TAT ATT
1756 TAA TTT TGA CAT AAG TAA CTT TTA AAA TTT GTC TTA AAA ATT TAT ACA CCA GCA ATT TAG
1816 ACA AAG CCT TAA GCA AAT TTT GTA TTA TTG TTC TCA CTT ATT ATT AAT AAT GAA GTA GAA
1876 GTT ACT TAA TTG CCA GCA AAT AAA TAC GTG TCA AAA AAG AAT CTG TAT TCA GAC CCC TGG
1936 GGT CAG GAA ATT ACT GCC CCA CTT GTC AAG TTC AGC CCA CCA TCT GTT TGA ACA TTA TAT
1996 GAA GTT TAA ATT CTA GTG TCC ATA AAT AAA GTT TCA GCG GCA CCC AAA AAA AAA AAA AAA
2056 AAA AAA
```

Non-denaturing Immunoprecipitation with polyclonal
rabbit α-p33 antiserum +/- preadsorption with GST-p33

(-) α-p33
(+) α-p33 preadsorbed with GST-p33 fusion protein
$M_r$ molecular weight standards

METHOD OF MODULATING P53 ACTIVITY

CROSS REFERENCE TO RELATED APPLICATIONS

This application claims priority under 35 U.S.C. §§119 and/or 365 to U.S. Application Serial No. 60/060,138 filed Sep. 26, 1997 and is a continuation of U.S. application Ser. No. 09/006,783 filed Jan. 14, 1998; now U.S. Pat. No. 6,297,366 the entire content of which is hereby incorporated by reference.

This invention was made with government support under R01 60730 and R03-TW00475 from the National Institutes of Health. The government has certain rights in the invention.

FIELD OF THE INVENTION

This invention relates to a method for modulating the activity of the protein p53 in cells by the addition of a peptide or protein having p33$^{ING1}$ biological activity or a nucleic acid coding for such a peptide or protein.

REFERENCES

The following references are cited in the application as numbers in brackets ([ ]) at the relevant portion of the application.
1. Levine, A. J., "The Tumor Suppressor Genes", *Annu. Rev. Biochem.*, 62:623–651 (1993).
2. Levine, A. J., "p53, the cellular gatekeeper for growth and division", *Cell*, 88:323–331 (1997).
3. International Patent Application No. W097/21809.
4. Sambrook, J., et al., "Molecular Cloning" (2nd Ed.), *A Laboratory Manual, Cold Spring Harbor Laboratory Press* (1989).
5. Harlow, E., et al., "Antibodies", *A Laboratory Manual, Cold Spring Harbor Laboratory* (1988).
6. Yang, Y., et al., "An approach for treating the hepatobiliary disease of cystic fibrosis by somatic gene transfer", *Proc. Nat'l. Acad. Sci. USA*, 90:4601–4605 (1993).
7. Atadja, P., et al., "Increased activity of p53 in senescing fibroblasts", *Proc. Nat'l. Acad. Sci. USA*, 92:8348–8352 (1995).
8. Atadja, et al., *Mol. Cell Biol.*, 14:4991–4999 (1994).
9. *Remington's Pharmaceutical Sciences*, 18th Ed. (1990).
10. Wong, H., et al., "Monitoring mRNA expression by polymerase chain reaction: the "primer-dropping" method", *Anal. Biochem.*, 223:251–258 (1994).
11. Shulman, et al., "A better cell line for making hybridomes secreting specific antibodies", *Nature*, 276:269–270, (1978).
12. Garkavtsev, et al., "Suppression of the novel growth inhibitor p33$^{ING1}$ promotes neoplastic transformation", *Nature*, 14:415–420 (1996).
13. Garkavtsev, et al., "Cellular localization and chromosome mapping of a novel candidate tumor suppressor gene", *Cytogenetics and Cell Genetics*, 76:176–178 (1997).
14. Garkavtsev and Riabowol, "Extension of the replicative life span of huma diploid fibroblasts by inhibition of the p33$^{ING1}$ candidate tumor suppressor", *Molecular and Cellular Biology*, 17:2014–2019 (1997).
15. Kane, et al., "Methylation of the hMLH1 promoter correlates with lack of expression of hMLH1 in sporadic colon tumors and mismatch repair-defective", *Cancer Res.*, 37:808–811 (1997).
16. Herman, et al., "Methylation specific PCR: a novel PCR assay for methylation status of CpG islands", *Proc. Natl. Acad. Sci. USA*, 93:9821–9826 (1996).
17. Chang, et al., "Gene Therapy: Applications to the Treatment of Gastrointestinal and Liver Diseases", *Gastroent.*, 106:1076–1084 (1994).

The disclosure of the above publications, patents and patent applications are herein incorporated by reference in their entirety to the same extent as if the language of each individual publication, patent and patent application were specifically and individually included herein.

BACKGROUND OF THE INVENTION

Many cancers originate and progress by accumulating mutations in one or more genes. Such mutations which result in cancer formation can be in proto-oncogenes or in tumor suppressor genes. Mutations in tumor suppressor genes result in loss of function, and therefore act in a recessive fashion to native genes. Oncogenes, in contrast, act in dominant fashion to native alleles and, therefore, are not usually inherited through the germ lines. The tumor suppressor genes, however, are found in inherited predispositions to cancer and are inherited as a dominant predisposition because of the high frequency of a second genetic event such as reduction in homozygosity [1].

Several tumor suppressor genes have been identified. Examples include the Rb gene, which is involved in retinoblastoma and osteosarcoma; p53, which is involved in osteosarcoma and adrenocortical, breast and brain cancers; WT-1, which is involved in Wilms' tumor, nephroblastoma and neurofibromatosis; adenomatous polyposis coli (APC), which is involved in adenomatous polyposis; and deleted colorectal cancer (DCC), which is involved with a somatic mutation in the colon.

The p53 protein is a transcription factor that enhances the rate of transcription of six or seven known genes that carry out, at least in part, the p53-dependent functions in a cell. These genes include p21, WAF1, Clp1, MDM2, GADD45, Cyclin G, Bax and IGF-BP3. P53 has also been shown to bind to c-Abl and enhance c-Abl's transcriptional activity. The p53 protein has also been shown to bind to an RNA polymerase II basal transcription factor TFIIH. TFIIH consists of two helicases which are implicated in the disease xeroderma pigmentosum. The Wilms' tumor suppressor gene product, WT1, has been shown to associate with p53 when both are overexpressed in the same cell.

The human p53 protein contains 393 amino acids and has been divided structurally and functionally into four domains [2]. The first 42 amino acids at the N-terminus constitute a transcriptional activation machinery in positively regulating gene expression. Amino acids 13–23 in the p53 protein are identical in a number of diverse species and certain amino acids in this region have been shown to be required for transcriptional activation by the protein in vivo. The sequence-specific DNA binding domain of p53 is localized between amino acid residues 102 and 292. The native p53 is a tetramer in solution, and amino acid residues 324–355 are required for this oligomerization of the protein. The C-terminal 26 amino acids form an open domain composed of nine basic amino acid residues that bind to DNA and RNA readily with some sequence or structural preferences. There is evidence that the p53 protein requires a structural change to activate it for sequence specific binding to DNA. Deletion of the C-terminus domain activates site-specific DNA binding by the central domain.

Normally, in a cell, the p53 protein is kept at a low concentration by its relatively short half-life. The events or signals that activate p53 are mediated by several stressful events. Several different types of DNA damage can activate p53, including double-stranded breaks in DNA produced by γ-irradiation and the presence of DNA repair intermediates after ultraviolet irradiation or chemical damage to DNA. This results in a rapid increase in the level of p53 in the cell and the activation of p53 as a transcription factor. In addition to DNA damage, hypoxia is able to stimulate p53 levels and activate the p53 protein. If ribonucleoside triphosphate pools fall below a critical threshold then p53 is also activated [2]. 53 mutations are found in 50–55% of all human cancers.

These mutations strongly select for p53 proteins that fail to bind to DNA in a sequence-specific fashion. It is clear that wild-type p53 acts to reduce the incidence of cancers by mediating apoptosis in cells with activated oncogenes. The treatment of neoplasia using radiation and chemotherapy results in extensive DNA damage and the activation of wild-type p53 in those cells. It is becoming clear that p53-dependent apoptosis can modulate the toxic effects of anticancer agents.

It would be advantageous to identify factors or proteins which enhance the activity of the wild-type p53 gene.

The gene ING1 (formerly called $p33^{ING1}$) described in International Patent Application No. WO97/21809 [3] and in Garkavtsev [12–14], represents a new tumor suppressor gene which is expressed in normal mammary epithelial cells, but only expressed at lower levels in several cancerous mammary epithelial cell lines and is not expressed in many primary brain tumors. The gene produces a 33 kD protein called $p33^{ING1}$. The amino acid sequence of the $p33^{ING1}$ related proteins $p28^{ING1}$ and $p26^{ING1}$ have been disclosed in U.S. application Ser. No. 09/006,783 filed Jan. 14, 1998.

SUMMARY OF THE INVENTION

This invention relates to the discovery that the protein $p33^{ING1}$ and related proteins, including $p28^{ING1}$ and $p26^{ING1}$ bind to p53 in vivo and activate p53 as a transcription factor in acute cotransfection assays. Thus, the invention provides methods for using $p33^{ING1}$ related proteins to enhance or inhibit the biochemical activity of p53.

The present invention is directed to a method of modulating the activity of p53 in a cell by administering an effective amount of a peptide having $p33^{ING1}$ biological activity to the cell.

In another method aspect the present invention is directed to a method of modulating the activity of p53 in a cell by administering an effective amount of a nucleic acid encoding a peptide having $p33^{ING1}$ biological activity to the cell. The nucleic acid may be DNA or RNA.

In a further aspect the present invention is directed to a method for isolating p53 comprising obtaining a biological sample containing p53; contacting said biological sample with a peptide having $p33^{ING1}$ biological activity under conditions wherein the p53 binds to the peptide; and isolating the p53 bound to the peptide.

In another aspect, this invention is directed to a method for detecting the presence of p53 in a sample comprising obtaining a biological sample suspected of containing p53; contacting said biological sample with a peptide having $p33^{ING1}$ biological activity under conditions wherein the p53 binds to the peptide; and detecting the presence of p53 bound to the peptide.

In yet a further aspect, the invention provides methods of diagnosing a malignant or premalignant condition in a human by obtaining a cell or tissue sample from the human; assaying the sample to determine ING1 gene expression in the sample; comparing ING1 gene expression in the sample with ING1 gene expression in a nonmalignant human cells or tissue; and assaying the sample to determine p53 gene expression in the sample; wherein a malignant or premalignant condition is diagnosed when both p53 and ING1 gene expression in the sample is less than p53 or ING1 gene expression in the nonmalignant human cells or tissues.

In a still further aspect, the invention provides methods of screening a human sample to detect a malignant or premalignant condition by obtaining a cell or tissue sample from the human; assaying the sample to determine ING1 gene expression in the sample; comparing ING1 gene expression in the sample with ING1 gene expression in a nonmalignant human cells or tissue; and assaying the sample to determine p53 gene expression in the sample; wherein a malignant or premalignant condition is detected when both p53 and ING1 gene expression in the sample is less than p53 or ING1 gene expression in the nonmalignant human cells or tissues.

In still another aspect, the invention provides methods of assessing a human sample to determine a risk of developing a malignant or premalignant condition by obtaining a cell or tissue sample from the human; assaying the sample to determine ING1 gene expression in the sample; comparing ING1 gene expression in the sample with ING1 gene expression in a nonmalignant human cells or tissue; assaying the sample to determine p53 gene expression in the sample; wherein a risk for developing a malignant or premalignant condition is determined to exist when both p53 and ING1 gene expression in the sample is less than p53 or ING1 gene expression in the nonmalignant human cells or tissues.

In a yet still further aspect, the invention provides pharmaceutical compositions useful for modulating p53 activity comprising an effective amount of at least one selected from the group consisting of a peptide or protein having $p33^{ING1}$ biological activity and a nucleic acid coding for a peptide or protein having $p33^{ING1}$ biological activity, wherein said effective amount is sufficient to provide effective modulation of p53 activity.

BRIEF DESCRIPTION OF THE DRAWINGS

FIG. 1 sets forth the complete cDNA sequence of ING1 (SEQ ID NO: 1) and the predicted amino acid sequence (SEQ ID NO:2) of $p33^{ING1}$

FIG. 5 illustrates that the Tag oncoprotein can inactivate the growth inhibitory effect of $p33^{ING1}$.

DETAILED DESCRIPTION OF THE INVENTION

Figure 2:
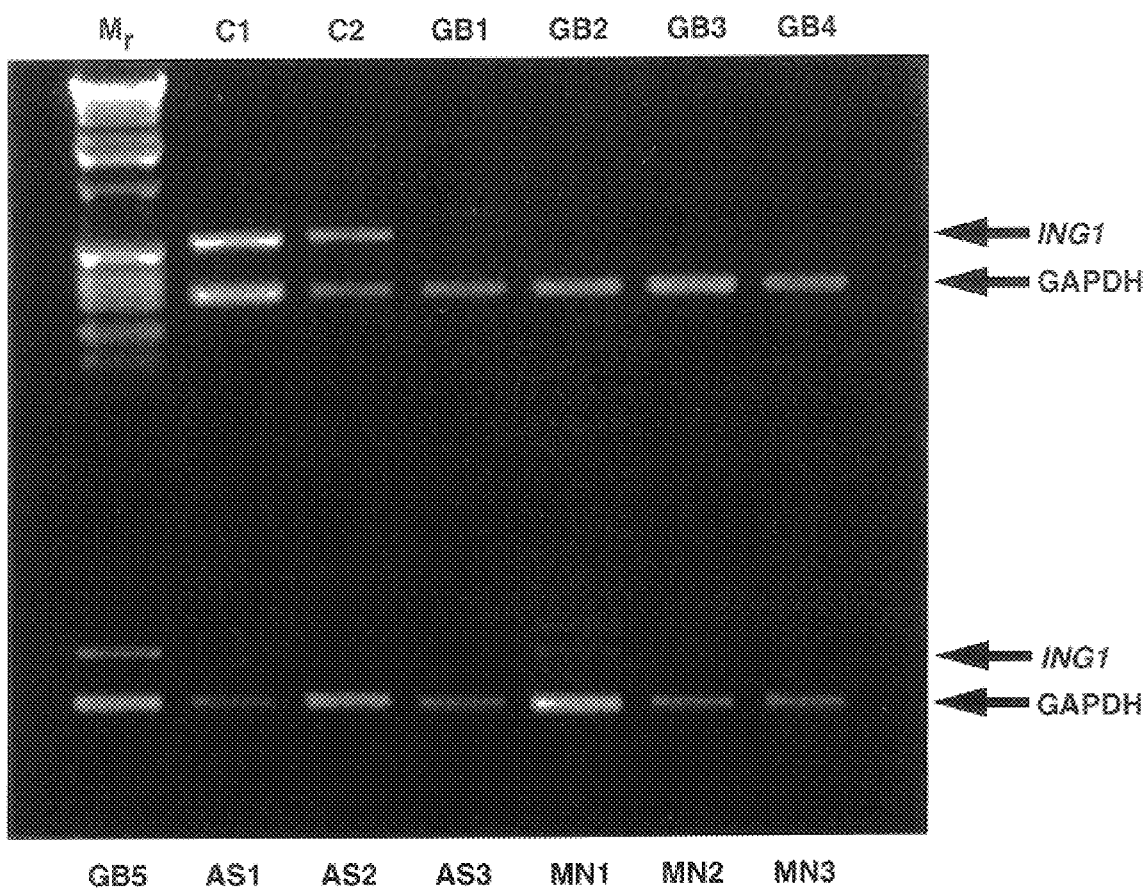
FIG. 2 illustrates the level of ING1 mRNA in control (c) tissue, glioblastoma (GB), astrocytoma (AS) and meningioma (MN) tumors as determined by RT-PCR.

The present invention relates to the discovery that the biological effects of ING1 and p53 gene expression are interrelated and require the activity of both genes. Specifically, we have discovered that neither of these two genes can, on it's own, cause growth inhibition when the other one is suppressed. Expression of both genes in a mammalian cell results in normal growth regulation anchorage-dependent growth and apoptosis as a response to irreversible DNA damage and other cellular insult. Inhibition of expression of either gene results in a loss of cellular growth control, anchorage-independent growth, inhibition of apoptosis and resistance to radiation and cytotoxic drugs.

Furthermore, a key mechanism of p53-mediated growth control, activation of transcription of certain cellular genes (such as the WAF1 gene), depends on the expression of ING1. In addition, a physical association between p33$^{ING1}$ and p53 proteins is disclosed as detected by immunoprecipitation. These results indicate that p33$^{ING1}$ is a component of the p53 signaling pathway that cooperates with p53 in negative regulation of cell proliferation by modulating p53-dependent transcriptional activation. Biological function of p53 signaling pathway can therefore be regulated (both enhanced or suppressed) by modulating p33$^{ING1}$ activity.

Expression of exogenous ING1 cDNA introduced into cells expressing p53 produces arrest of the cells in the G1 phase of the cell cycle. Several cell types respond to introduction and expression of ING1 cDNA with apoptosis, and ING1 gene expression has been found to be up regulated (i.e., increased) in senescent human fibroblasts [17]. Inhibition of ING1 expression by antisense RNA (such as a genetic suppressor element (GSE)) promotes anchorage independent growth in mouse breast epithelial cells, increases the frequency of focus formation of NIH 3T3 cells, and prolongs the life span of diploid human fibroblasts in culture.

In addition, the key role of p33$^{ING1}$ in the p53 signaling pathway opens the possibility of regulation of this pathway activity by modulating p33$^{ING1}$ activity. Such regulation may involve enhancement or restoration of p53 function by increasing the activity of p33$^{ING1}$, or suppression of p53 function by inhibition of p33$^{ING1}$. Stimulation or restoration of the p53 pathway is critically important for the efficacy of anti-cancer therapy, while suppression of p53 pathway can be used to defend sensitive tissues from genotoxic stress and for the generation of immortal cell lines also requiring p53 functional inactivation. All the above applications can be achieved by modulation of p33$^{ING1}$ activity, as an alternative to modulation of the activity of p53 itself. The discovery that p33$^{ING1}$ is an essential component of p53 signaling pathway provides a novel approach to regulation of the p53 pathway in mammalian cells.

Thus, this invention is based in the finding that cell growth inhibition is mediated at least in part by the expression of p33$^{ING1}$ in mammalian cells, i.e., cell growth decreases as expression of p33$^{ING1}$ increases, and cell growth increases as expression of p33$^{ING1}$ decreases. The invention described herein also relates to the discovery that a novel tumor suppressor protein, designated p33$^{ING1}$, is capable of binding to and activitating the tumor suppressor gene p53.

A. Definitions

As used herein the following terms have the following meanings:

"Antibody" means a molecule that binds to a known antigen. An "anti-p33$^{ING1}$ antibody" means an antibody molecule that binds to one or more epitopes of the p33$^{ING1}$ protein. The antibody may be a polyclonal or a monoclonal antibody.

"Antisense" and "Antisense nucleotides" means DNA or RNA constructs which block the expression of the naturally-occurring gene product. For example, in the present invention, use of a DNA construct that produces ING1 antisense RNA blocks the expression of p33$^{ING1}$ by destroying or inactivating ING1 mRNA.

"Biological sample" means a sample of mammalian cells. These cells may be part of a tissue or organ sample obtained, for example, by biopsy, or they may be individual cells, for example, blood cells or cells grown in tissue culture.

"Cancerous cell" means a cell in or from a neoplasm. Preferably the cancerous cells is breast cancer, brain cancer, gastric cancer, haematologic neoplasms and head and neck squamous cell carcinomas.

"Breast cancer" means any of various malignant neoplasms of the breast or mammary tissue.

"Brain cancer" means any of various malignant neoplasms of the brain, neuroglial cells or meninges.

"Cell cycle" means the cyclic biochemical and structural events occurring during growth of cells. The cycle is divided into periods called : $G_0$, $Gap_1$, ($G_1$), DNA synthesis (S), $GAP_2$ ($G_2$), and mitosis (M).

"Cell division" means mitosis, i.e., the usual process of cell reproduction.

"Code" or "encode", when used with reference to a nucleotide's relation to a protein, mean the system whereby particular combinations of adjacent nucleotides control the insertion of particular amino acids in equivalent places in a protein molecule.

"Expression" means the production of a protein or nucleotide in the cell.

"Growth" means progression through the cell cycle with the result that two daughter cells are formed from each mother cell. "Actively growing" means that state wherein cells exhibit growth and cell division.

"Growth inhibition phenotype" is intended to encompass a pleiotropic phenotype in a mammalian cell, including but not limited to growth inhibition (including contact inhibition), cellular aging and senescence, apoptosis, sensitivity to radiation and cytotoxic drugs, and anchorage-dependent growth.

"Label" means to incorporate into a compound a substance that is readily detected. Such substances include radioactive substances and fluorescent dyes, for example.

"Mammalian cell" means a cell in or from a mammal, either in a tissue or organ or in tissue culture.

"Neoplasia" means the process resulting in the formation and growth of an abnormal tissue that grows by cellular proliferation more rapidly than normal, and continues to grow after the stimuli that initiated the new growth cease.

"Neoplastic" describes the abnormal tissue that grows by cellular proliferation more rapidly than normal, and continues to grow after the stimuli that initiated the new growth cease.

"Normal cell" means a non-cancerous cell.

"Proliferation" means growth and reproduction, i.e., division of cells.

"Native" means the nucleic acid of a non-mutated or wild-type gene or peptide sequence encoded by such a gene as found in a phenotypically normal cell.

"Substantially identical" means that the polynucleotide or nucleic acid of interest is able to hybridize to the complement of the known sequence under stringent conditions. Such stringent conditions preferably require at least 60% identity, more preferably the conditions require at least 80% identity and most preferably the conditions require at least 90% identity.

When used in relation to peptides and proteins, "substantially identical" means that the amino acid sequence of the peptides share at least 85% identity, more preferably at least 90% identity and most preferably at least 95% identity.

B. Methodology

A gene, called ING1 for Inhibitor of Growth, was previously isolated (U.S. patent application Ser. No. 08/751,230, filed Nov. 15, 1996 entitled, "DNA Sequence Encoding the Suppressor Gene ING1", which is a continuation-in-part of U.S. patent application Ser. No. 08/569,721, filed Dec. 8, 1995, both of which are incorporated by reference in their entirety herein). The 33 kDA protein encoded by ING1 is a potent growth inhibitor in both acute and chronic assays which expressed in the sense orientation and promotes focus formation in NIH3T3 cell, growth in soft agar of NMuMg cells and extends the proliferative life span of diploid human fibroblasts which expression of ING1 is reduced to 10% of wild-type expression using antisense constructs.

It has been found that the protein p33$^{ING1}$ binds p53 in vivo and activates p53 as a transcription factor in acute cotransfection assays.

The present invention is directed to a method of modulating the activity of p53 in a cell by administering an effective amount of a peptide having p33$^{ING1}$ biological activity to the cell. The present invention is also directed to a method of modulating the activity of p53 in a cell by administering an effective amount of a nucleic acid encoding a peptide having p33$^{ING1}$ biological activity to the cell. The nucleic acid may be DNA or RNA.

The present invention is directed to a method for isolating p53 comprising obtaining a biological sample containing p53; contacting said biological sample with a peptide having p33$^{ING1}$ biological activity under conditions wherein the p53 binds to the peptide; and isolating the p53 bound to the peptide. In particular, the present invention is directed to a method of isolating p53 capable of binding to p33$^{ING1}$.

This invention is also a method for detecting the presence of p53 in a sample comprising obtaining a biological sample suspected of containing p53; contacting said biological sample with a peptide having p33$^{ING1}$ biological activity under conditions wherein the p53 binds to the peptide; and detecting the presence of p53 bound to the peptide. In particular, the present invention is directed to a method of detecting p53 capable of binding to p33$^{ING1}$.

It is expected that several p33$^{ING1}$-related peptides will be useful in the present invention. In particular, p33$^{ING1}$, its analogs and related proteins and peptides which are effective in binding to p53 are preferred.

Included within the scope of the p33$^{ING1}$, as that term is used herein, are p33$^{ING1}$ s having the amino acid sequence set forth in FIG. 1, glycosylated or deglycosylated derivatives of p33$^{ING1}$, homologous amino acid sequence variants of the sequence of FIG. 1, and homologous in vitro-generated variants and derivatives of p33$^{ING1}$, which are capable of exhibiting a biological activity in common with the p33$^{ING1}$ of FIG. 1. Preferably the peptides comprise from about 10–20 amino acids more preferably from 10–40 amino acids and most preferably from 10–100 amino acids.

p33$^{ING1}$ biological activity is defined as either: (1) immunological cross-reactivity with at least one epitope of native p33$^{ING1}$, or (2) the possession of at least the ability to bind p53 in common with native p33$^{ING1}$s.

Immunologically cross-reactive, as used herein, means that the candidate polypeptide is capable of competitively inhibiting the qualitative biological activity of the native p33$^{ING1}$ having this activity, with polyclonal antisera raised against the known active analog. Such antisera are prepared in conventional fashion by injecting goats or rabbits, for example, subcutaneously with the known active analog in complete Freund's adjuvant, followed by booster intraperitoneal or subcutaneous injection in incomplete Freund's.

This invention is concerned with amino acid sequence variants of native p33$^{ING1}$ Amino acid sequence variants of the p33$^{ING1}$ are prepared with various objectives in mind, including increasing the affinity of the p33$^{ING1}$ for its binding partner, facilitating the stability, purification and preparation of the p33$^{ING1}$, modifying its biological half-life, improving therapeutic efficacy, and lessening the severity or occurrence of side effects during therapeutic use of the p33$^{ING1}$.

Amino acid sequence variants of the p33$^{ING1}$ fall into one or more of three classes: insertional, substitutional, or deletional variants. These variants ordinarily are prepared by site specific mutagenesis of nucleotides in the DNA encoding the p33$^{ING1}$, by which DNA encoding the variant is obtained, and thereafter expressing the DNA in recombinant cell culture. However, variant p33$^{ING1}$ fragments having up to about 100 to 150 amino acid residues are prepared conveniently by in vitro synthesis. The p33$^{ING1}$ variants typically exhibit the same qualitative biological activity as naturally occurring p33$^{ING1}$.

While the site for introducing an amino acid variation may be predetermined, the mutation, per se, need not be predetermined. For example, in order to optimize the performance of a mutation at a given site, random or saturation mutagenesis (where all 20 possible residues are inserted) is conducted at the target codon and the expressed p33$^{ING1}$ variant is screened for the optimal combination of desired activities. Such screening is within the ordinary skill of the art.

Amino acid insertions will usually be on the order of from about one to about ten amino acid residues; substitutions are typically introduced for single residues and deletions will range from about one to about thirty residues. Deletions or insertions preferably are made in adjacent pairs. That is, a deletion of two residues or insertion of two residues. Substitutions, deletions, insertions or any combination thereof may be introduced or combined to arrive at a final construct.

Insertional amino acid sequence variants of the native p33$^{ING1}$ are those in which one or more amino acid residues extraneous to native p33$^{ING1}$ are introduced into a predetermined site in the target p33$^{ING1}$ and which displace the pre-existing residues. Commonly, insertional variants are fusions of heterologous proteins or polypeptides to the amino or carboxyl terminus of the p33$^{ING1}$. Such variants are referred to as fusions of the p33$^{ING1}$ and a polypeptide containing a sequence which is other than that which is normally found in the p33$^{ING1}$ at the inserted position. Several groups of fusions are contemplated for carrying out the invention described herein.

Immunologically active p33$^{ING1}$ derivatives and fusions comprise the p33$^{ING1}$ and a polypeptide containing a non-p33$^{ING1}$ epitope. Such immunologically active derivatives and fusions of p33$^{ING1}$ are within the scope of this invention. The non-p33$^{ING1}$ epitope may be any immunologically competent polypeptide, i.e., any polypeptide which is capable of eliciting an immune response in the animal in which the fusion is to be administered, or which is capable of being bound by an antibody raised against the non-p33$^{ING1}$ polypeptide.

Substitutional variants are those in which at least one residue in the FIG. 1 sequence has been removed and a different residue inserted in its place. Novel amino acid sequences as well as isosteric analogs (amino acid or otherwise) are included within the scope of this invention.

Some deletions, insertions and substitutions will not produce radical changes in the characteristics in the p33$^{ING1}$ molecule. However, while it is difficult to predict the exact effect of the substitution, deletion or insertion in advance of doing so, for example, when modifying an immune epitope on the p33$^{ING1}$ protein, one skilled in the art will appreciate that the effect will be evaluated by routine screening assays. For example, a change in the immunological character of the p33$^{ING1}$ protein, such as affinity for a given antibody, is measured by a competitive-type immunoassay. Modifications of protein properties such as redox or thermal stability, hydrophobicity, susceptibility to proteolytic degradation, or the tendency to aggregate with carriers or into multimers may be assayed by methods well known to one of skill in the art.

Deletions of cysteine or other labile amino acid residues may also be desirable. For example, they may increase the oxidative stability of the p33$^{ING1}$ protein. Deletion or substitution of potential proteolysis sites, e.g., Arg Arg, is accomplished by deleting one of the basic residues or substituting one with glutaminyl or histidyl residues.

The ability of a p33$^{ING1}$ peptide to bind p53 can be determined through a number of association assays, such as non-denaturing immunoprecipitation assays, immunoprecipitation western assays, yeast 2 hybrid expression system assays and immuno-co-localization assays.

In a non-denaturing immunoprecipitation assay, p53 is labeled with a radioactive label such as [$^{35}$S-]methionine. The labeled p53 is contacted with the p33$^{ING1}$ peptide or native p33$^{ING1}$ protein and an antibody to p33$^{ING1}$ under non-denaturing conditions. The antibody mixture is then contacted with Protein A Sepharose. The Protein A Sepharose binds the anti-p33$^{ING1}$ antibody and whatever proteins or peptides, including the p33$^{ING1}$ peptide, that are bound to the anti-p33$^{ING1}$ antibody. If p53 is bound to the p33$^{ING1}$ peptide, then the p53 will be bound to the protein A sepharose. The protein A sepharose is separated from the mixture and the proteins bound to the sepharose isolated. The presence of p53 in the bound proteins indicates that the p33$^{ING1}$ peptide is capable of binding p53.

In an immunoprecipitation western assay, p53 is mixed with the p33$^{ING1}$ peptide or protein and an antibody to p33$^{ING1}$ under non-denaturing conditions. The antibody mixture is then contacted with Protein A Sepharose. The Protein A Sepharose binds the anti-p33$^{ING1}$ antibody and whatever proteins, including p33$^{ING1}$, that are bound to the anti-p33$^{ING1}$ antibody. If p53 is bound to the p33$^{ING1}$ peptide, then the p53 will be bound to the protein A sepharose. The protein A sepharose is separated from the mixture and the proteins bound to the sepharose isolated and run on a denaturing gel. The gel is electroblotted to a membrane and the membrane is probed with antibodies against p53. The presence of the antibodies may be detected directly using labeled antibodies or indirectly using antibodies linked to enzymes. If p53 is present on the membrane then the p33$^{ING1}$ peptide is capable of binding p53.

Other methods for determining the ability of the p33$^{ING1}$ peptide to bind to p53 are by the Yeast 2 hybrid system and immuno-co-localization studies.

The ability of a p33$^{ING1}$ peptide to activate p53 can be determined through a number of functional assays, such as coexpression with a reporter gene or testing whether the peptide will inhibit growth in the presence of p53.

In one assay, increasing amounts of p53 are placed in the presence of a reporter gene such a luciferase or chloramphenical acetyl transferase (CAT) functionally attached to a promoter, such as the p21 promoter, to which p53 binds and activates transcription. The level of expression of the reporter gene is measured in the presence of the p53 protein. Next the same amount of p53 and differing amounts of the p33$^{ING1}$ peptide or protein are placed in contact with the reporter gene functionally attached to the promoter. If the p33$^{ING1}$ peptide activates the p53 protein, then the level of expression of the reporter gene should increase concomitantly with increasing amounts of the p33$^{ING1}$ peptide.

In another assay, the p33$^{ING1}$ peptide is placed in a cell having wild-type p53 to see whether growth of the cell is inhibited. Growth will be inhibited if the p33$^{ING1}$ peptide is activating the p53 protein. If the p33$^{ING1}$ peptide is placed in a cell in which the p53 protein is mutant or absent, growth of the cell should not be inhibited.

In another assay, a cell line having wild-type p53 and p33$^{ING1}$ is infected with a retrovirus vector having the ING1 gene placed in an antisense orientation such that antisense ING1 mRNA is produced inhibiting the expression of p33$^{ING1}$ protein and then evaluate whether the growth of the cells increases.

Antibodies to the p33$^{ING1}$ may be prepared in conventional fashion [5] by injecting goats or rabbits, for example, subcutaneously with the complete p33$^{ING1}$ protein or a peptide consisting of at least 10 amino acids similar to the p33$^{ING1}$ protein in complete Freund's adjuvant, followed by booster intraperitoneal or subcutaneous injection in incomplete Freund's adjuvant. The anti-p33$^{ING1}$ antibodies may be directed against one or more epitopes on p33$^{ING1}$. Monoclonal antibodies against p33$^{ING1}$ can be prepared by methods known in the art [5]. The antibodies are preferably labeled with a marker, for example, with a radioactive or fluorescent marker. It is contemplated that the antibodies would be labeled indirectly by binding them to an anti-goat or anti-rabbit antibody covalently bound to a marker compound.

In alternative embodiments, the diagnostic methods of the invention also include the steps of assaying a cell or tissue sample for expression of p53 as well as expression of p33$^{ING1}$. Antibodies specific for p53 for detecting p53 protein are available in the art, as are specifically hybridizing sequences and amplification primers for detecting p53 mRNA expression, as disclosed in Ossovskaya, et al., 1996, *Proc. Natl. Acad. Sci. USA,* 93:10309–10314 (incorporated by reference).

C. Pharmaceutical Compositions

In one embodiment the p33$^{ING1}$ protein or a peptide having p33$^{ING1}$ biological activity is introduced directly. In a preferred embodiment the peptide possesses the ability to bind p53 in common with native p33$^{ING1}$.

In another embodiment nucleotides coding for p33$^{ING1}$ or a peptide having p33$^{ING1}$ biological activity are introduced by retroviral or other means. In one embodiment the nucleotide coding for p33$^{ING1}$ comprises a nucleotide sequence which codes for the amino acid sequence of p33$^{ING1}$ as set forth in FIG. 1. Preferably the nucleotide sequence is substantially identical to the cDNA sequence of FIG. 1.

For the purposes of this invention, a recombinant expression construct is a replicable DNA construct in which a DNA sequence encoding a GSE or amino acid sequence is operably linked to suitable control sequences capable of effecting the expression of the encoded amino acids in a suitable host. For the purposes of this invention, the term "operably linked" is intended to indicate that the nucleic acid components of the recombinant expression construct are linked, most preferably covalently linked, in a manner and orientation that the nucleic acid sequences encoding a GSE or amino acid sequence of the alternative splice variant or truncated version thereof are under the control of and respond to the transcriptional, replication and other control elements comprising the vector construct when introduced into a cell, preferably a mammalian cell and most preferably a human cell. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook, et al., 1990, *Molecular Cloning: A Laboratory Manual*, Cold Spring Harbor Press: New York.

Additional vectors for preparing the recombinant expression constructs of the invention include plasmids, viruses (including phage), retroviruses, and integratable DNA fragments (i.e., fragments integrated into the host genome by homologous recombination). The vector replicates and functions independently of the host genome, or may, in some instances, integrate into the genome itself. Suitable vectors will contain replicon and control sequences which are derived from species compatible with the intended expression host. Suitable vectors also comprise additional or alternative selectable marker sequences, such as sequences conferring resistance to hygromycin or other antibiotic substances, or sequences encoding a gene that complements a cellular deficiency (such as thymidine kinase or dihydrofolate reductase). Viral or plasmid vectors may be used to deliver sense and antisense constructs to target cells in vivo. Such viral vectors may include retroviruses, adenovirus or adenovirus-associated viruses. Such vectors, recombinant expression constructs and methods are known in the art [6,17].

Parenteral administration of the nucleic acids is preferred with subdermal or intramuscular administration most preferred. Intravenous administration or use of implanted milliosmol pumps (available from Alza) may also be used.

When used for parenteral administration, which is preferred, the nucleic acids of the present invention may be formulated in a variety of ways. Aqueous solutions of the nucleic acids of the present invention may be encapsulated in polymeric beads, liposomes, nanoparticles or other injectable depot formulations known to those of skill in the art. (Examples thereof may be found, for example, in Remington's [9].) The nucleic acids may also be encapsulated in a viral coat. Doses are selected to provide effective modulation of p53 activity such as activation of p53.

The methods of this invention may also be achieved by using a pharmaceutical composition comprising one or more of the following cancer cell proliferation inhibiting compounds: p33$^{ING1}$, its analogs and related proteins and peptides. Doses are selected to provide effective modulation of p53 activity to result in, e.g., inhibition of cancer cell growth and/or proliferation.

Parenteral administration of the proteins or peptides is preferred, with subdermal or intramuscular administration most preferred. Intravenous administration or use of implanted milliosmol pumps (available from Alza) may also be used.

When used for parenteral administration, which is preferred, the proteins and peptides of the present invention may be formulated in a variety of ways. Aqueous solutions of the proteins or peptides of the present invention may be encapsulated in polymeric beads, liposomes, nanoparticles or other injectable depot formulations known to those of skill in the art. (Examples thereof may be found, for example, in Remington's [9].)

Compositions including a liquid pharmaceutically inert carrier such as water may also be considered for both parenteral and oral administration. Other pharmaceutically compatible liquids may also be used. The use of such liquids is well known to those of skill in the art. (Examples thereof may be found, for example, in Remington's [9].)

The dose level and schedule of administration may vary depending on the particular p33$^{ING1}$-related compound(s) and/or compositions used, the method of administration, and such factors as the age and condition of the subject.

As discussed previously, parenteral administration is preferred, but formulations may also be considered for other means of administration such as orally, per rectum, and transdermally. The usefulness of these formulations may depend on the particular compound used and the particular subject receiving the p33$^{ING1}$-related compound.

Oral formulations of p33$^{ING1}$-related compounds may optionally and conveniently be used in compositions containing a pharmaceutically inert carrier, including conventional solid carriers, which are conveniently presented in tablet or capsule form. Formulations for rectal or transdermal use may contain a liquid carrier that may be oily, aqueous, emulsified or contain certain solvents suitable to the mode of administration. Suitable formulations are known to those of skill in the art. (Examples thereof may be found, for example, in Remington's [9].)

EXAMPLES

The methods described as follows were used to perform the studies described herein. In addition, the generally known methods set forth in laboratory manuals for molecular cloning and antibody techniques [e.g., 4,5] may advantageously be used by one of skill in the art to produce additional embodiments of the invention.

Example 1

Expression of a GST-p33$^{ING1}$ Fusion Protein and Creation of Anti-p33$^{ING1}$ Polyclonal Antibody In order to generate polyclonal antibodies, a fragment of ING1 containing nucleotides 161–1146 of FIG. 1 was subcloned into the EcoRI-XhoI sites of the bacterial expression vector pGEX-KG (Pharmacia Biotech, Inc., Quebec, Canada) containing the glutathione-binding portion of glutathione-S-transferase (GST). Plasmids were sequenced to verify that the correct reading frame was obtained and the constructs were electroplated into *E.coli* XL1-Blue in order to express the encoded glutathione-S-transferase-p33$^{ING1}$ (GST-p33) fusion protein. Following selection, bacterial cultures were induced to express the fusion protein by the addition of 0.1 mM isopropyl thio-galactopyranoside (IPTG). After induction, the pelleted bacteria were washed several times with MTPBS (150 mM NaCl, 16mM Na$_2$HPO$_4$, 4mM NaH$_2$PO$_4$ pH7.3), sonicated (5×, 3–10 sec. bursts), repelleted and mixed with 5× Laemmli sample buffer (2 mL per 1 mL of pellet).

The fusion protein was purified by standard glutathione-agarose column affinity chromatography. Eluted GST-p33$^{ING1}$ fusion protein was dialyzed and used as an immunogen in female New Zealand white rabbits. After four boosters, rabbits were bled and their serum tested for reactivity against the fusion protein. All animals showed reactivity and the bleeds showing the highest titer were chosen for subsequent use in Western blot, immunoprecipitation and immunofluorescence protocols.

Example 2

Production and Selection of the Monoclonal Antibody

Four 5 to 6 week old female BALB/c mice were each injected intraperitoneally with 10 μg of GST-p33 from Example 1 in Freund's complete adjuvant for the first injection, and with 10 μg of GST-p33 in Freund's incomplete adjuvant for subsequent injections at 3 week intervals. Serum titers were determined by ELISA and the mouse with the best titer was boosted intraperitoneally 5 days prior to the fusion.

On the day of the fusion the spleen was removed from the mouse and spleen cells were isolated. The spleen cells were combined with Sp2/mIL6 cells in the presence of polyethylene glycol 1500. Sp2/mIL6 is a genetically engineered myeloma line produced by incorporating mouse interleukin-6 genes into Sp2/0 cells which results in much higher yields of fused, and therefore drug resistant, cells in subsequent steps [11]. The fused cells were combined with media containing hypoxanthine aminopterin thymidine (HAT) and the resulting mixture was plated out into 96 well plates to isolate colonies.

Fusion wells were tested for titer by the use of ELISA. At approximately 10 to 14 days, 100 μl of supernatant was removed from fusion wells containing colonies and added to a GST-p33-coated well in a 96 well ELISA plate. Supernatant was removed and the wells were incubated with goat anti-mouse IgG-biotin, washed, incubated with strepavidin-alkaline phosphatase, washed and developed with para-nitrophenylphosphate in substrate buffer and read at $OD_{405}$. Initial positives were retested against both GST-p33 and GST alone to determine cross-reactivity, then the resulting positives were cloned twice more following the procedure above. The final positives were grown up into larger volumes and concentrated supernatants were collected for use.

Example 3

Alterations of ING1 Levels in Cancer Cell Lines and Tumor Tissues

Normal diploid control cell strains and brain and breast cancer cell lines and tumors were analyzed by RT-PCR analysis. Reverse transcription with total RNA from each of the cell lines was performed.

The relative levels of ING1 transcript were compared to the internal control gene glyceraldehyde-3-phosphate dehydrogenase (GAPDH) using PCR primers specific for the $p33^{ING1}$ and GAPDH genes. ING1 and GAPDH were amplified in the same reaction tube using the "primer dropping" approach [10] which internally controls for efficiency of reverse transcription and amplification by PCR.

Reverse transcription (RT) with 1 μg of total RNA from the cells was performed using 50 U of RNasin (Pharmacia Biotech, Inc., Quebec, Canada) and 200 U of MMLV reverse transcriptase for 50 min. at 42° C. in 20 μl reaction volumes. Two μl of each RT reaction was amplified using 2 U of Taq polymerase. The two sets of primer pairs for the ING1 gene and for the GAPDH gene that were used, were: 5'-GAAGCGGCGGATGCTGCACT-3'(SEQ ID NO: 3); and 5'-ACGCACGAGAAGTGGAACCA-3'(SEQ ID NO: 4) for the ING1 1 gene and 5' CGGAGTCAACGGATTTG-GTCGTAT -3'(SEQ ID NO: 5); and 5'-AGCCTTCTCCATGGTGGTGAAGAC 3'(SEQ ID NO: 6) for the GAPDH gene. Thirty two PCR cycles for ING1 and twenty two PCR cycles for GAPDH were performed using standard conditions [4]. Primers for GAPDH were added to PCR tubes at the end of the 10th cycle [10].

The levels of ING1 mRNA were estimated by scanning densitometry.

FIG. 2 illustrates the RT-PCR results of glioblastoma (lanes GB1–GB4) astrocytoma (lanes AS1–AS3) and meningioma (MN1–MN3) primary tumors as compared to two control brain samples (C1–C2). The ING1 mRNA was expressed at considerably lower levels, or not expressed at all, in the glioblastomas, astrocytomas and meningiomas as compared to the normal brain cells. The ethidium bromide-stained agarose gel shows primary data indicating that significant levels of $p33^{ING1}$ expression are seen in normal brain tissue but that expression is undetectable in many tumors. The gene also appears to be undergoing a rearrangement in the sample labelled MN1.

Example 4

Binding of $p33^{ING1}$ to p53

Figure 3:
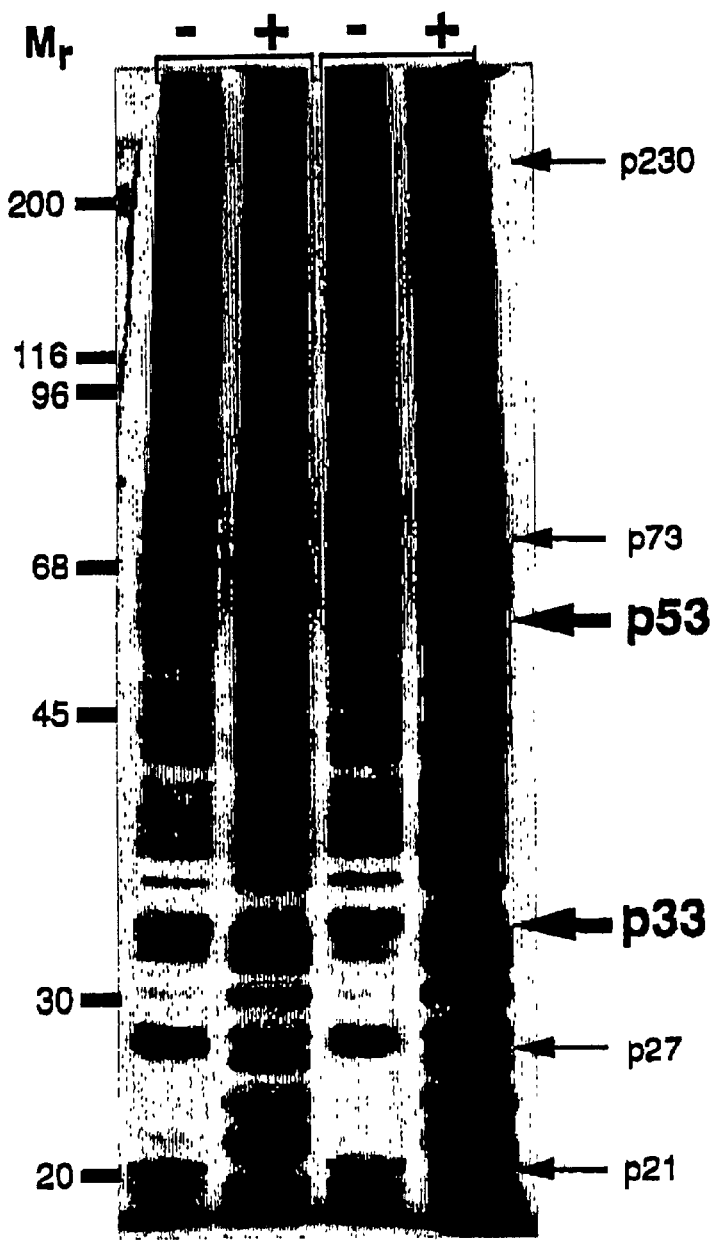
FIG. 3 illustrates the binding of the $p33^{ING1}$ protein to the p53 protein.

Total cell lysate from normal human diploid fibroblasts (Hs68) [ATCC CRL1635] labeled with $[^{35}S]$-methionine was immunoprecipitated under nondenaturing conditions with the polyclonal rabbit anti-$p33^{ING1}$ raised against a GST-p33 fusion protein described in Example 1. Lanes marked + indicate immunoprecipitations in which antibodies were preadsorbed with unlabeled GST-p33 protein to prevent interaction with endogenous labeled $p33^{ING1}$ and serve as negative controls. Following the completion of immunoprecipitations as described previously (8), immunoprecipitates were electrophoresed through a 12% polyacrylamide gel, impregnated with 1 M sodium salicylate, dried and exposed to X-ray film for 4 days at −80C. using an intensifying screen. Bars on the left indicate the migration position of commercial methylated migration standards and arrows on the right highlight bands that are specifically recognized by the $p33^{ING1}$ antiserum. FIG. 3 illustrates that $p33^{ING1}$ binds with a polypeptide of 53 kDa that incorporates $[^{35}S]$-methionine rapidly.

Example 5

Immunoprecipitation of $p33^{ING1}$ with p53

Six plates of the Hs68 normal primary diploid fibroblast strain [ATCC CRL1635] at high passage level were harvested in RIPA buffer under non-denaturing conditions (no ionic detergents were used) and lysates were equally aliquoted into four separate Eppendorf tubes, on ice. Hybridoma supernatants (100 microliters each) for p53 (PAb 421, DO-1, PAb 240 [Calbiochem, LaJolla, CA]) and for GST (a negative control) were added to each tube and the tubes were rocked at 4 C.° for 4 hours. Tubes were pelleted at 14,000 x g for 1 minute at 4 C.° and supernatants were transferred to fresh tubes. Twenty microliters of Protein G Sepharose (PGS) were added to each tube and the contents were rocked for 30 minutes at 4 C.°. Tubes were gently pelleted (2 second "pop spins"), supernatants were aspirated and the pellets were washed with 1 ml of ice-cold RIPA buffer. This washing procedure was repeated 4 times before the PGS pellets were suspended in 35 microliters of 2× Laemmli sample buffer, boiled 2 minutes and the products of the immunoprecipitation electrophoresed through a 15% polyacrylamide gel together with pre-stained protein markers. Proteins in the gel were electroblotted onto PVDF membranes for 1 hour at 25 volts at room temperature and the membrane was blocked overnight in PBS containing 10% nonfat milk and 2% fetal bovine serum (PBS+). After blocking, the membrane was incubated with a 1:500 dilution of polyclonal rabbit anti-GST-$p33^{ING1}$ in PBS+, washed twice in TBS-0. 1% Tween-20, incubated with a 1:1000 dilution of commercially available goat anti-rabbit IgG-biotin in PBS +, washed as above, incubated with a 1:1000 dilution of Strepavidin-HRP in PBS + and washed 2 times as described above and once in TBS. Equal parts of chemiluminescent substrates (Amersham) were mixed together and applied to the blot. The blot was then exposed to Kodak X-Omat film for from ½ to 10 minutes in the dark to visualize bound $p33^{ING1}$ in different immunoprecipitations.

Figure 4:
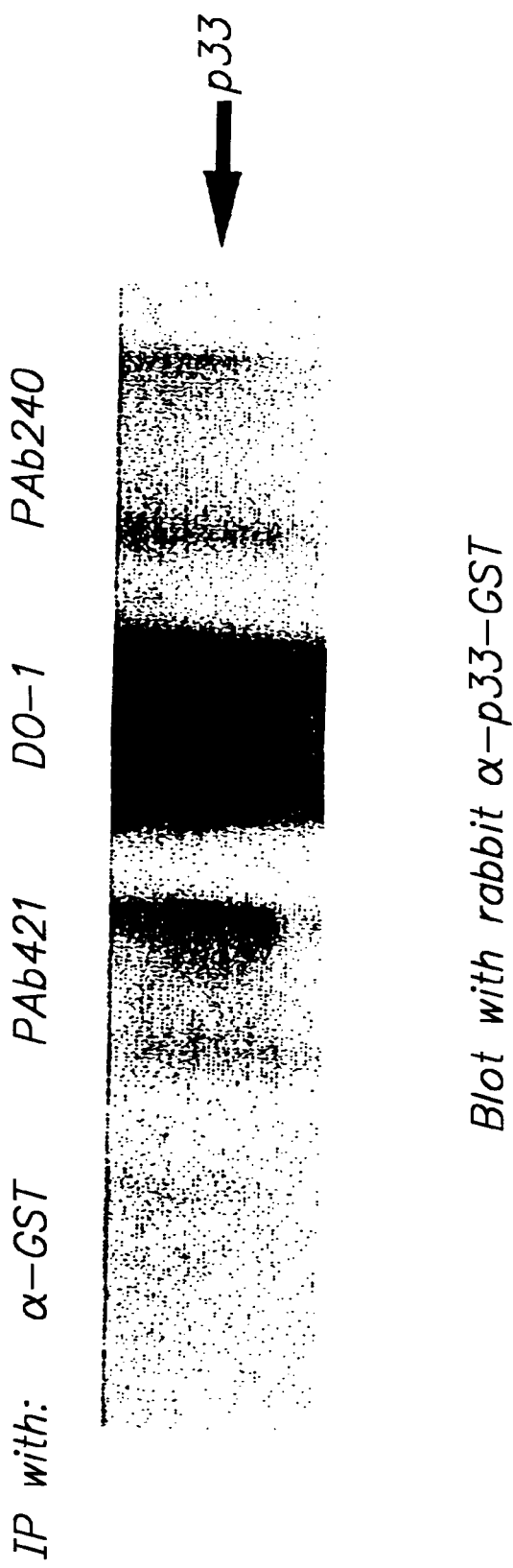
FIG. 4 illustrates the immunoprecipitation of $p33^{ING1}$ with p53.

As seen in FIG. 4, the GST-negative control showed no signal for $p33^{ING1}$ However, the DO-1 antibody which binds to the $NH_2$ terminus of p53 showed a strong signal, the PAb 421 antibody, which recognizes the carboxyl terminus of p53 showed a very weak signal and the additional negative control PAb 240 which recognizes mutant p53 showed no signal. This suggests that the $p33^{ING1}$ protein binds to the carboxyl terminus of p53 which is consistent with a role in activating the protein.

Example 6

Suppression of the Growth-inhibitory Effect of $p33^{ING1}$ by SV40

Figure 5A:
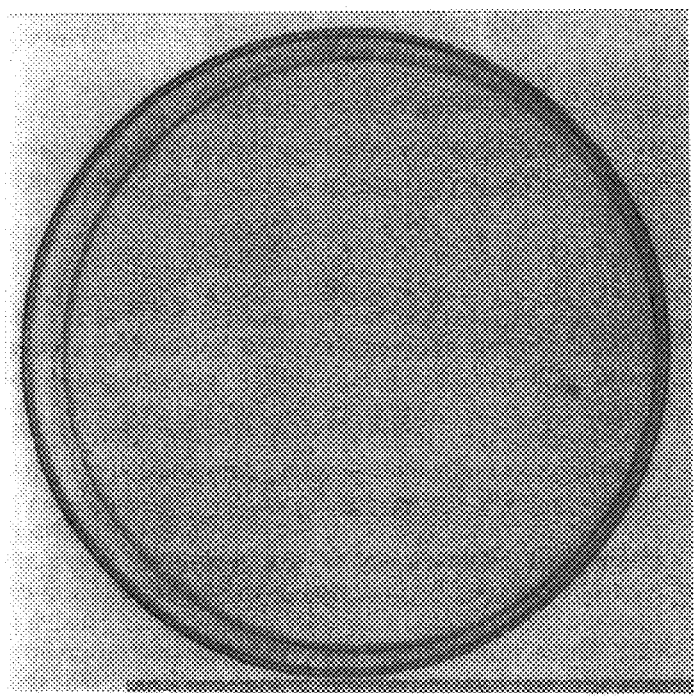
FIG. 5A is W138 cells transfected with PBK-ING1-S.
Figure 5B:
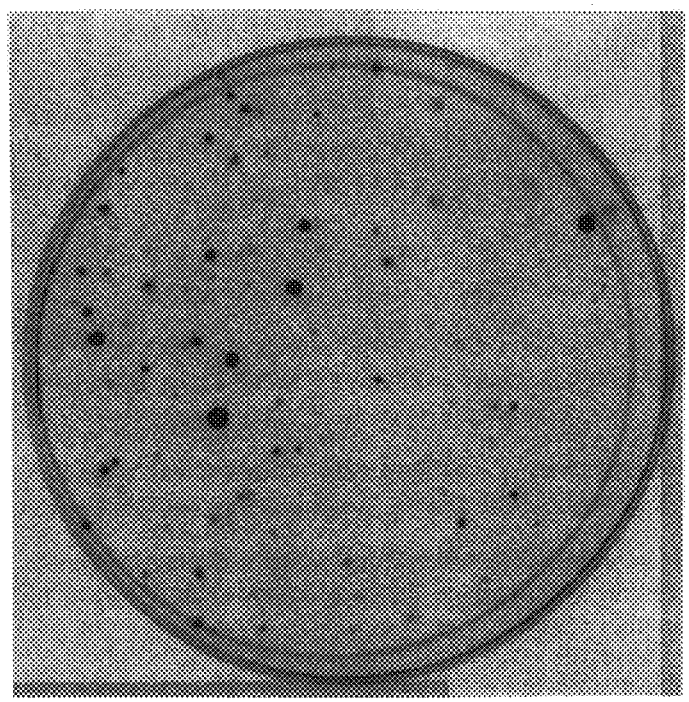
FIG. 5B is VA13 cells transfected with PBK-ING1-S.

It had been found that overexpression of $p33^{ING1}$ efficiently blocked cell growth (Garkavtsev [12]) similar to observations made upon the overexpression of the tumor suppressors p53 and Rb. The SV40 oncoprotein Tag contains a site that binds and inactivates both the p53 and Rb tumor suppressors. This experiment tests whether Tag could also block the growth-inhibitory effect of $p33^{ING1}$. The ING1 gene was cloned in the sense orientation into the mammalian expression vector pBK, which contains a neomycin resistance gene and a cytomegalovirus promoter. The resulting construct, pBK-ING1-S was transfected into both normal human diploid fibroblasts (W138) and a syngeneic line immortalized by SV40 (VA13). Following growth of the cells in G418 antibiotic-containing medium for 3 weeks the plates were fixed and stained with Coomassie brilliant blue to identify surviving colonies. A large number of stable transformants were recovered from the VA13 cells transfected with pBK-ING1-S (FIG. 5B), whereas very few colonies were seen in plates of W138 cells transfected with pBK-ING1-S (FIG. 5A). These preliminary results suggest that the SV40 Tag oncoprotein can inactivate the growth-inhibitory effect of $p33^{ING1}$ in a manner similar to that seen with p53 and Rb via binding and inactivation of p53.

Example 7

Mutation Status of Primary Brain Cancers

Mutation does not appear to be the major mechanism by which cancer cells inactivate $p33^{ING1}$ as determination of the expression levels of $p33^{ING1}$ in different cancer types is beginning to show. The statistically significant numbers of samples of cancer types which have been examined are the primary brain cancers (glioblastomas, astrocytomas and meningiomas), breast cancers and neuroblastomas.

The level of ING1 mRNA was determined by RT-PCR by the method set forth in Example 3. Of 65 brain tumors examined, ING1 mRNA was not detected by RT-PCR in 36, indicating total loss of $p33^{ING1}$ expression in 55% of brain tumor samples. All of these samples were internally controlled for RNA quality and RT-PCR efficiencies. This is a minimal estimate of the proportion of brain tumors in which $p33^{ING1}$ is shut off since if samples were even modestly contaminated with normal brain tissue they would score as positive in our RT-PCR assay. Table I shows data for $p33^{ING1}$ mutation status and expression for 42 samples. The degree of methylation of the ING gene was determined by the methods similar to those set forth in Kane, et al. [15] and Herman, et al. [16]. To determine mutations present in the ING1 gene single stranded conformational polymorphism assays (SSCP) were used.

Three pairs of primers were used to amplify the majority of the ING1 gene. These primer pairs were as follows:

I.

A. SSCP2 primer CTGAAGGAGCTAGACGAGTG SEQ ID NO:7

B. RIII primer GGCTTGTCAGACTGCGCTAC SEQ ID NO:8

II.

A. RI primer GTAGCGCAGTCTGACAAGCC (nucleotides 474–494 of SEQ ID NO: 1)

B. RV primer ACGCACGAGAAGTGGAACCA SEQ ID NO:4

III.

A. SSCPI primer GACAACGACGAGTGCCCCAT SEQ ID NO:9

B. RIV primer CTACCTGTTGTAAGCCCTCTCT SEQ ID NO: 10

TABLE 1

| Patient | Age/Sex | Tumor type | Tumor grade | RNA exp. | ING1 analysis Methylation | Mutation | p53 RNA exp. |
|---|---|---|---|---|---|---|---|
| 29 | 64/M | GBM | IV | − | M | ND | + |
| 36 | 40/M | GBM | IV | + | − | − | + |
| 41 | 72/F | GBM | IV | + | − | − | + |
| 69 | 41/M | GBM | IV | − | M | ND | + |
| 18 | 42/F | GBM | IV | − | M | ND | + |
| 51 | 59/F | GBM | IV | − | M | ND | + |
| 30 | 53/M | GBM | IV | − | M | ND | + |
| 83 | 53/M | GBM | IV | + | − | − | + |
| 90 | 66/M | GBM | IV | + | − | − | + |
| 205 | 19/M | GBM | IV | − | M | ND | + |
| 34 | 66/M | GBM | IV | − | M | ND | + |
| 35 | 63/M | GBM | IV | − | M | ND | + |
| 42 | 16/M | GBM | IV | + | − | − | + |
| 78 | 62/M | GBM | IV | + | − | − | + |
| 30 | 53/M | GBM | IV | + | − | − | − |
| 32 | 48/F | GBM | IV | − | M | ND | − |
| B24 | 60/F | GBM | IV | − | M | ND | + |

TABLE 1-continued

| Patient | Age/Sex | Tumor type | Tumor grade | RNA exp. | Methylation | Mutation | p53 RNA exp. |
|---|---|---|---|---|---|---|---|
| | | | | ING1 analysis | | | |
| 140 | 67/F | GBM | IV | + | – | – | + |
| 146 | 53/M | GBM | IV | + | – | – | + |
| 55 | 45/M | GBM | IV | – | M | ND | + |
| B76 | 60/F | GBM | IV | + | – | – | + |
| B78 | 64/F | GBM | IV | – | M | ND | + |
| B149 | 72/M | GBM | IV | + | – | – | + |
| B154 | 51/M | GBM | IV | – | M | ND | + |
| B156 | 82/M | GBM | IV | + | – | – | + |
| B161 | 47/M | GBM | IV | – | M | ND | + |
| B172 | 66/F | GBM | IV | + | – | – | + |
| B175 | 58/M | GBM | III | – | M | ND | + |
| B178 | 67/M | GBM | II | + | – | – | – |
| 141 | 41/M | astrocytoma | III | + | – | – | – |
| 11 | 58/M | astrocytoma | III | – | M | ND | + |
| 27 | 29/M | astrocytoma | III | – | M | ND | + |
| 71 | 10/F | astrocytoma | III | – | M | ND | y+ |
| 48 | 75/F | meningioma | – | + | – | (Arg to His) | + |
| 21 | 75/F | meningioma | – | – | M | ND | + |
| 23 | 45/M | meningioma | – | – | M | ND | + |
| B4 | 60/M | meningioma | – | – | M | ND | + |
| B5 | 60/F | meningioma | – | – | M | ND | + |
| B7 | 68/F | meningioma | – | + | – | – | + |
| B39 | 86/M | meningioma | – | – | M | – | + |
| B47 | 66/F | meningioma | – | – | M | – | + |
| B38 | 67/F | meningioma | – | + | – | – | + |

Results suggest that p33$^{ING1}$ expression is also repressed in a significant number of breast cancers and neuroblastomas.

Example 8

Growth Suppressive Effect of p33$^{ING1}$ Depends on the Status of p53

In order to assess the relatedness of p33 and p53 expression in controlling growth and proliferation in mammalian cells, the effects of expressing the p33$^{ING1}$ related proteins p28$^{ING1}$ and/or p26$^{ING1}$ in cells differing in the status of p53 gene expression were assayed. It was expected that expression of ING1 would result in growth inhibition of the cells if the effects of ING1 were independent of p53 gene expression.

Cloned p28$^{ING1}$ (SEQ ID No: 11) and/or p26$^{ING1}$ (SEQ ID NO: 13; same sequence as amino acids 85 to 294 of SEQ ID NO: 2-encoding DNA was introduced into cells by retroviral transduction of either the truncated version of ING1 cDNA, the alternative splice variant of ING1 cDNA, or an antisense-oriented ING1 cDNA fragment (anti-ING1 GSE) comprising nucleotides 942–1124 of the ING1 cDNA sequence (SEQ ID No: 12), which acts as a potent inhibitor of p33$^{ING1}$ expression. Suppression of colony formation by ING1 overexpression was evident only in the cells that maintained wild type p53, including human diploid skin fibroblasts, primary mouse embryo fibroblasts and rat REF52 cells. After ING1 transduction, surviving cells expressed very low levels of p28$^{ING1}$, as determined by immunohistochemical staining and Western blot analysis. However, retroviral transduction of ING1 resulted in no growth suppressive effect in cells having inactivated p53. ING1-expression did not inhibit colony formation in human fibroblasts carrying a homozygous deletion of p53 (Li-Fraumeni fibroblasts, cell line MDAH041, obtained from George Stark), nor in mouse embryo fibroblasts and REF52 cells that expressed a carboxyl-terminal portion of p53 (comprising GSE 56, as disclosed in Ossovskaya, et al., 1996, *Proc. Natl, Acad. Sci. USA*, 93:10309–10314, incorporated by reference), that is a strong inhibitor of p53 function. In all cells tested, transduced ING1 was expressed at high levels. These results indicated that cell growth inhibition mediated by p28$^{ING1}$ or p26$^{ING1}$ expression required co-expression of p53.

In another series of experiments, the effect of p28$^{ING1}$ expression was observed in a human fibrosarcoma cell line, HT1080 (available from the American Type Culture Collection). HT1080 cells ($10^5$ cells per well of a 6-well plate) transduced with different retroviral constructs were incubated in the presence of different concentrations of etoposide for 4 days. Cell viability was then determined using the MTT assay (Pauwels, et al., 1988, *J. Virol. Methods*, 20:309–321). The experiment was repeated 3 times using 3 parallel wells for each drug concentration. In contrast to the result obtained with "normal" fibroblasts described above, overexpression of p28$^{ING1}$ in these cells had only a minor negative effect on colony growth under normal cell culture conditions. However, p28$^{ING1}$ expression strongly increased sensitivity of these cells to DNA damaging agents such as the chemotherapeutic drug etoposide or gamma irradiation. This effect was also found to be p53-dependent, since co-expression of the p53 suppressor GSE56 with p28$^{ING1}$ inactivated the sensitizing effect of DNA damaging agents produced in these cells by p28$^{ING1}$ expression alone. These results are consistent with results showing that loss of p53 expression leads to resistance to radiation and chemotherapeutic drugs due to suppression of apoptosis (see Lowe, et al., 1993, *Cell*, 74:957–967).

These observations indicate that the growth inhibitory effect of p28$^{ING1}$ or p26$^{ING1}$ expression requires wild type p53 gene expression and suggested that the ING1 gene product could act either "upstream" of or in cooperation with p53.

Example 9

Growth Suppressive Effect of p53 Depends on the $p33^{ING1}$

The results disclosed above showed that the growth-inhibiting function of $p33^{ING1}$ required the co-expression of p53 in mammalian cells. These results indicated that it was necessary to determine the converse: whether the phenotype associated with p53 expression—growth arrest and/or apoptosis—required co-expression of $p33^{ING1}$.

In these experiments, variants of p53 deficient derivatives of mouse Balb/c 3T3 cells (termed 10(1)cells) were prepared that differed dramatically in $p33^{ING1}$ expression. One variant was transduced with the pLNCX retroviral vector alone, thereby expressing the endogenous amount of mouse $p33^{ING1}$. Another variant was transduced with the pLNCX retroviral vector encoding human $p28^{ING1}$, so that these cells expressed both the endogenous mouse $p33^{ING1}$ and the transduced human $p28^{ING1}$. The third variant was transduced with the pLNCX retroviral vector encoding the anti-ING1 GSE (SEQ ID No: 1), so that expression of the endogenous mouse $p33^{ING1}$ was suppressed in these cells. Expression status of $p33^{ING1}/p28^{ING1}$ in each of these cell variants was determined by immunofluorescence staining using a chemiluminescence-labeled sandwich assay comprising a polyclonal rabbit anti-$p33^{ING1}$ antibody as primary antibody, a biotinylated donkey anti-rabbit antibody as secondary antibody, and horseradish peroxidase-conjugated streptavidin (Amersham, Arlington Heights, Ill.).

Into these cells was transduced a retroviral vector encoding a hygromycin resistance gene and either wild type p53 protein or a nonfunctional mutant, $p53^{175His}$ (as disclosed in Kopnin, et al., 1995, *Oncol. Res.*, 7:299–306). The cells were found to be highly sensitive to expression of exogenously-added p53 cDNA. Wild type p53 gene expression inhibited cell growth in variants expressing endogenous mouse $p33^{ING1}$ and the combination of mouse $p33^{ING1}$ and human $p28^{ING1}$. However, expression of p53 in cells co-expressing the anti-ING1 GSE were not growth-inhibited, and produced multiple colonies upon culturing incubation. These results were expected, since the results of the experiments described in Example 8 indicated that p53 required functional $p33^{ING1}$ in order to mediate growth inhibition.

In contrast, no cell growth suppression was observed in any of the variants expressing the non-functional p53 mutant, $p53^{175His}$. Each of the variant cell cultures showed robust growth after transduction with retroviral vector encoding this mutant p53 species. These results, and in particular the results obtained with the variants expression either the endogenous mouse $p33^{ING1}$ or both the endogenous $p33^{ING1}$ and the transduced human $p28^{ING1}$ showed that the growth-suppressing activity of $p33^{ING1}$ requires co-expression of functional p53.

Cell rescue from the growth inhibitory effect of p53 by ING1 antisense RNA (i.e., GSE) expression was confirmed in co-transfection experiments. 10(1) cells were transfected using the calcium phosphate method (see Ossovskaya, et al., 1996, *Proc. Natl. Acad. Sci. USA*, 93:10309–10314) with a plasmid encoding wild type p53 and either a vector encoding the anti-ING1 GSE, the anti-p53 GSE termed GSE56 (see Ossovskaya, et al., ibid.) or the vector alone and selected in 200 μg/mL hygromycin. Expression of p53 with the anti-ING1 GSE resulted in no observed growth suppression. Similarly, growth suppression was not observed in cells co-transfected by p53 and GSE56. In the cells expressing the p53 plasmid (and the endogenous mouse $p33^{ING1}$), growth suppression was observed.

These results indicated that both p53 and ING1 must be co-expressed in mammalian cells to confer the growth suppression phenotype on the cells, and suggested that p53 and $p33^{ING1}$ act cooperatively in mediating the growth suppression phenotype.

Example 10

$p33^{ING1}$ is a mediator of transcriptional activation by p53

In view of the results obtained in Examples 8 and 9 above, mammalian cells were assayed to determine the role of $p33^{ING1}$ in transcriptional activation of p53-responsive genes. The growth inhibitory effect of p53 was known to be mediated by transcriptional activation of a p53-responsive inhibitor of cyclin-dependent kinases, $p21^{WAF1}$ (see El Deiry, et al., 1993, *Cell*, 75:817–825). To analyze the effect of ING1 expression on this important function of p53, a series of experiments were performed using a reporter expression construct in which the bacterial gene for chloramphenicol acetyltransferase (CAT) was under the control of a combination of a p53-responsive binding site from the WAF1 gene promoter with the minimal heat shock Hsp70 (see Kondratov, et al., 1996, *Molecular Biology* (Russia), 30:613–620).

These cells were prepared as follows. $2 \times 10^5$ cells per 60-mm dish were transfected with a total of 12 μg of plasmid DNA containing 4 μg of pWAF1-CAT and 2 μg of pCMV-lacZ. Cell extracts were prepared by freezing and thawing and were normalized for protein content. The efficiency of transfection was determined by using a quantitative β-galactosidase assay.

Two different cell lines expressing by wild type p53 gene (human HT1080 and rat REF52), and the p53-deficient Balb/c 3T3 cell line 10(1) described above, were transfected with the reporter plasmid in combination with plasmids expressing either ING1 cDNA (encoding $p28^{ING1}$), anti-ING1 GSE, a dominant negative p53 mutant genetic suppressor element (GSE56), or with control insert-free plasmid. For experiments performed using the p53-deficient 10(1) cells, plasmid expressing wild type p53 cDNA was also added. Extracts from the transfected cells were prepared and CAT assays performed using conventional techniques (see Sambrook, et al., ibid.).

10(1) cells transfected with and expressing p53+GSE56, p53+anti-ING1 GSE, GSE56, anti-ING1 GSE, ING1 or the vector alone showed no detectable CAT activity, consistent with the absence of p53 activity in these cells. CAT activity was detected in cells expressing p53, either alone (p53 or p53+vector) or co-expressed with exogenously-added human $p28^{ING1}$ (p53+ING1). p53-dependent CAT activity in transfected cells was stimulated 2–4-fold in the presence of the ING1-expressing construct (p53+ING1) and significantly inhibited (3–5 fold) by ING1 antisense GSE. The inhibitory effect of the anti-ING1 GSE was comparable to that of anti-p53 GSE56. Similar results were obtained with the other cell lines tested. These results indicated that the function of p53 as a transcriptional activator depends on the presence of $p28^{ING1}$, and suggested that the growth inhibition activity associated with ING1 gene expression involves stimulation of p53 transcriptional activity.

Expression of the endogenous WAF1 gene is also affected by ING1 expression. HT1080 cells overexpressing ING1 cDNA (resulting from transfection with the $p28^{ING1}$- encoding plasmid disclosed above) contains 4–6 times more WAF1 mRNA than control cells. RNA was isolated from HT1080 cells transfected with the p28$^{ING1}$-encoding plasmid or vector alone and assayed by Northern Blot hybridization (Sambrook, et al., ibid.) probed with a radiolabeled WAF1 cDNA probe; a radiolabeled GAPDH probe was included in the hybridization as a loading control. In the autoradiograms, the amount of WAF1 mRNA on the Northern Blot is greater in the lanes containing RNA isolated from cells transfected with the p28$^{ING1}$-encoding plasmid than in the lanes containing RNA isolated from cells transfected with the plasmid vector alone. This difference is retained even in gamma-irradiated HT1080 cells that induce WAF1 expression by a p53-dependent mechanism.

These results demonstrated that ING1 expression is required for the transcriptional activation mediated by p53, and that overexpression of ING1 gene product increases the degree of transcriptional activation in cells expressing p53.

Example 11

Physical Interaction of p33$^{ING1}$ and p53 Proteins

The close association of the biochemical activities of p53 and p33$^{ING1}$ suggested that these proteins are capable of physically interation, for example, by forming a complex between the 2 types of molecules. In order to determine whether the functional interdependence of p53 and p33$^{ING1}$ was accompanied by physical interaction between the molecules, co-immunoprecipitation experiments were performed as follows. Cells growing in 100-mm tissue culture dishes (containing approximately 3×10$^6$ cells per dish) were washed with ice-cold phosphate buffered saline (PBS), scraped into 1 mL of RIPA buffer (see Harlow & Lane, 1988, *Antibodies: A Laboratory Manual*, Cold Spring Harbor Laboratory Press: New York, p.447) not containing detergents such as SDS and sonicated. The extracts were cleared by centrifugation at 10,000 g for 10 minutes. A mixture of Pab421 and DO-1 monoclonal antibodies were added to cell extract and incubated for 2 hours at 4° C. 30 μL of protein A Sepharose equilibrated in RIPA were then added and incubated for additional 30 minutes. The beads were extensively washed with ice-cold RIPA and the precipitate was dissolved in a sample buffer for electrophoresis and Western Blot analysis. Western Blotting was performed, using the anti-GST-p33$^{ING1}$ rabbit polyclonal antibodies against a bacterially expressed gluthatione-S-transferase-p33$^{ING1}$ fused protein (prepared as disclosed in International Application, Publication No. WO97/21809, incorporated by reference) or a mixture of anti-p53 monoclonal antibodies produced by hybridomas Pab421 and DO1 (provided by Arnold Levine). Biotinylated donkey anti-rabbit or sheep anti-mouse antibodies were used by secondary ones. Antibody binding was visualized by enhanced chemiluminescence using horseradish peroxidase conjugated with streptavidin (Amersham).

In these experiments, anti-p53 antibodies (Pab421 and DO1) were used to precipitate p53-containing protein complexes from cellular extracts. The presence of p33$^{ING1}$ protein in these precipitates was monitored by immunoblotting with polyclonal antibodies against p33$^{ING1}$. Several cell types, differing in p53 expression levels, were assayed, including: wild type human skin fibroblasts (HSF), growing under normal conditions or treated with the chemotherapeutic drug Adriamycin to induce p53 stabilization; human fibroblasts from a patient with Li-Fraumeni syndrome (line MDAH041), which lack expression of p53; and a derivatives of MDAH041 carrying a tetracycline-regulated wild type p53 cDNA (TR9-7; see Agarwal, et al., 1995, *Proc. Natl. Acad. Sci. USA*, 92:8493–8497); in TR9-7 cells maintained in the presence of 1 μg/mL of tetracycline, p53 expression is suppressed, which p53 expression is induced by incubation without tetracycline for 24 hours. All these cells expressed similar levels of p33$^{ING1}$, indicating that p33$^{ING1}$ expression was not affected by p53 expression or drug-induced DNA damage, p33$^{ING1}$ protein was detected in anti-p53 antibody precipitates in all the cells expressing wild type p53 (HSF, HSF+Adriamycin, and TR9-7 cells), and the amount of p33$^{ING1}$ in precipitates correlated with the p53 content. In contrast, no p33$^{ING1}$ protein was found in anti-p53 antibody precipitates from the extracts of p53-null MDAH041 cells, consistent with the lack of p53 expression in these cells. In similar experiments, a polyclonal antisera against p33$^{ING1}$ co-precipitated a 53 KDa protein from an extract of $^{35}$S-methionine labeled cells expressing wild type p53 but not from the p53-null cells, thus confirming physical association between p53 and p33$^{ING1}$.

Taken together, the results disclosed in the above Examples herein demonstrated that p33$^{ING1}$/p28$^{ING1}$ (collectively termed "ING1 gene expression") directly cooperates with p53 in growth regulation by modulating the ability of p53 to act as a transcriptional activator. Reduction of ING1 gene expression was found to inhibit the growth suppressive activity of p53, suggesting that p33$^{ING1}$ is essential for p53 function. The mechanism of p33$^{ING1}$/p53 cooperation involves physical interaction between these 2 proteins, which form a complex detectable by immunoprecipitation. These data places ING1 into a family of p53-interacting proteins, such a mdm2, Rb-1 and p300, which modulate p53 activity through physical interaction (see Momand, et al., 1992, *Cell*, 69:1237–1245; Jayaraman, et al., 1997, *Genes Devel.*, 11:558–570; Avantaggiati, et al., 1997, *Cell*, 89:1175–1184). The involvement of ING1 gene expression in the p53 signaling pathway points to ING1 as a new tumor suppressor gene whose loss or inactivation may contribute to altered cell growth, resistance to apoptosis, or establishment of the immortal phenotype in tumors retaining wild type p53.

Example 12

Diagnostic Assay

The existence of the ING1 tumor suppressor gene suggests that the phenotype of altered cell growth, resistance to apoptosis, or establishment of the immortal phenotype in tumors or premalignant cells, which has heretofore been associated with alterations in expression of p53, may occur even in cells in which the p53 gene continues to be expressed. Thus, the recognition that inhibition of ING1 expression is associated with certain type of clinical malignancy and with cellular growth control suggests that diagnostic assays determining ING1 gene expression levels are useful for assessing patient disease status or risk for developing malignant disease.

Diagnostics assays provided by the invention involve determining gene expression levels of p33$^{ING1}$/p28$^{ING1}$ in cell or tissue samples from an individual. In the practice of such assays, mRNA levels are determined using conventional assays including reverse transcription—polymerase chain reaction (RT-PCR; Kawasaki & Wang, ibid.), preferably quantitative embodiments thereof (see Noonan, et al., 1990, *Proc. Natl. Acad. Sci. USA*, 87:7160–7164), by standard filter hybridization procedures (including Northern Blot hybridization), or by RNase protection assay. In these assays, RNA is extracted from cells or tissue samples from a human to be tested, and the aforesaid assays performed, most preferably in parallel with similar assays either from normal cells or tissue of the individual, or with a panel of standardized cell lines expressing known amounts of $p33^{ING1}/p28^{ING1}$. Comparison of the ING1 gene expression levels in the cell or tissue sample from the human with ING1 gene expression levels in the normal cell or tissue sample from the human or the panel of standardized cell lines is used to determine whether ING1 gene expression is reduced or absent in the cell or tissue sample. A determination of reduced or absent ING1 gene expression is associated with malignancy or premalignancy in the individual, or with an increased risk of developing a malignant disease.

Alternatively, $p33^{ING1}/p28^{ING1}$ production in a cell or tissue sample from an individual is determined directly using antibodies produced against the ING1 gene product. Conventional immunoassays are used, preferably quantitative immunoassay (e.g., RIA or immunohistochemical assays) to determine the amount of the ING1 gene product that is present in the a sample. In the practice of this embodiment of the methods of the invention, immunoassay is performed on proteins extracted from the cell or tissue sample to be tested. Alternatively, immunostaining assays are used to detect $p33^{ING1}/p28^{ING1}$ expression in the cells or tissues tested. Polyclonal or monoclonal antibodies are useful in the diagnostic assays of the invention. Comparison of $p33^{ING1}/p28^{ING1}$ expression in the cell or tissue sample with expression in normal cells or tissue from the individual, or with a standardized panel of cell lines is performed to determine whether the tested cell or tissue sample has reduced or absent $p33^{ING1}/p28^{ING1}$ expression levels.

Modification of the above-described modes of carrying out various embodiments of this invention will be apparent to those skilled in the art following the teachings of this invention as set forth herein. The examples described above are not limiting, but are merely exemplary of this invention, the scope of which is defined by the following claims.

What is claimed is:

1. A method of modulating the activity of p53 in vitro to regulate gene transcription or cell proliferation in a cell by administering to the cell an effective amount of a nucleic acid encoding p28$^{ING1}$ (SEQ ID NO: 13).

2. A method of modulating the activity of p53 in vitro to regulate gene transcription or cell proliferation in a cell by administering to the cell an effective amount of a nucleic acid encoding p26$^{ING1}$ (SEQ ID NO: 11).

* * * * *

SEQUENCE LISTING

```
<160> NUMBER OF SEQ ID NOS:  13

<210> SEQ ID NO 1
<211> LENGTH: 2061
<212> TYPE: DNA
<213> ORGANISM: Human
<220> FEATURE:
<221> NAME/KEY: CDS
<222> LOCATION: (16)..(897)

<400> SEQUENCE: 1
gagtaacccg ataat atg ccg ttg tgc acg gcg acg aga att ccc aga tat        51
                Met Pro Leu Cys Thr Ala Thr Arg Ile Pro Arg Tyr
                 1               5                  10 agc agt agc agt gat ccc ggg cct gtg gct cgg ggc cgg ggc tgc agt        99
Ser Ser Ser Ser Asp Pro Gly Pro Val Ala Arg Gly Arg Gly Cys Ser
             15                  20                  25 tcg gac cgc ctc ccg cga ccc gcg ggg ccg gct cgg aga cag ttt cag       147
Ser Asp Arg Leu Pro Arg Pro Ala Gly Pro Ala Arg Arg Gln Phe Gln
         30                  35                  40 gcc gca tct ttg ctg acc cga ggg tgg ggc cgc gcg tgg ccg tgg aaa       195
Ala Ala Ser Leu Leu Thr Arg Gly Trp Gly Arg Ala Trp Pro Trp Lys
 45                  50                  55                  60 cag atc ctg aag gag cta gac gag tgc tac gag cgc ttc agt cgc gag       243
Gln Ile Leu Lys Glu Leu Asp Glu Cys Tyr Glu Arg Phe Ser Arg Glu
                 65                  70                  75 aca gac ggg gcg cag aag cgg cgg atg ctg cac tgt gtg cag cgc gcg       291
Thr Asp Gly Ala Gln Lys Arg Arg Met Leu His Cys Val Gln Arg Ala
             80                  85                  90 ctg atc cgc agc cag gag ctg ggc gac gag aag atc cag atc gtg agc       339
Leu Ile Arg Ser Gln Glu Leu Gly Asp Glu Lys Ile Gln Ile Val Ser
         95                 100                 105 cag atg gtg gag ctg gtg gag aac cgc acg cgg cag gtg gac agc cac       387
Gln Met Val Glu Leu Val Glu Asn Arg Thr Arg Gln Val Asp Ser His
        110                 115                 120 gtg gag ctg ttc gag gcg cag cag gag ctg ggc gac aca gtg ggc aac       435
Val Glu Leu Phe Glu Ala Gln Gln Glu Leu Gly Asp Thr Val Gly Asn
125                 130                 135                 140 agc ggc aag gtt ggc gcg gac agg ccc aat ggc gat gcg gta gcg cag       483
Ser Gly Lys Val Gly Ala Asp Arg Pro Asn Gly Asp Ala Val Ala Gln
                145                 150                 155
```

-continued

| | | |
|---|---|---|
| tct gac aag ccc aac agc aag cgc tca cgg cgg cag cgc aac aac gag<br>Ser Asp Lys Pro Asn Ser Lys Arg Ser Arg Arg Gln Arg Asn Asn Glu<br>　　　　　160　　　　　　　　165　　　　　　　　170 | 531 |
| aac cgt gag aac gcg tcc agc aac cac gac cac gac gac ggc gcg tcg<br>Asn Arg Glu Asn Ala Ser Ser Asn His Asp His Asp Asp Gly Ala Ser<br>　175　　　　　　　　180　　　　　　　　185 | 579 |
| ggc aca ccc aag gag aag aag gcc aag acc tcc aag aag aag aag cgc<br>Gly Thr Pro Lys Glu Lys Lys Ala Lys Thr Ser Lys Lys Lys Lys Arg<br>190　　　　　　　　195　　　　　　　　200 | 627 |
| tcc aag gcg aag gcg gag cga gag gcg tcc cct gcc gac ctc ccc atc<br>Ser Lys Ala Lys Ala Glu Arg Glu Ala Ser Pro Ala Asp Leu Pro Ile<br>205　　　　　　　　210　　　　　　　　215　　　　　　　　220 | 675 |
| gac ccc aac gaa ccc acg tac tgt ctg tgc aac cag gtc tcc tat ggg<br>Asp Pro Asn Glu Pro Thr Tyr Cys Leu Cys Asn Gln Val Ser Tyr Gly<br>　　　　　225　　　　　　　　230　　　　　　　　235 | 723 |
| gag atg atc ggc tgc gac aac gac gag tgc ccc atc gag tgg ttc cac<br>Glu Met Ile Gly Cys Asp Asn Asp Glu Cys Pro Ile Glu Trp Phe His<br>　240　　　　　　　　245　　　　　　　　250 | 771 |
| ttc tcg tgc gtg ggg ctc aat cat aaa ccc aag ggc aag tgg tac tgt<br>Phe Ser Cys Val Gly Leu Asn His Lys Pro Lys Gly Lys Trp Tyr Cys<br>255　　　　　　　　260　　　　　　　　265 | 819 |
| ccc aag tgc cgg ggg gag aac gag aag acc atg gac aaa gcc ctg gag<br>Pro Lys Cys Arg Gly Glu Asn Glu Lys Thr Met Asp Lys Ala Leu Glu<br>270　　　　　　　　275　　　　　　　　280 | 867 |
| aaa tcc aaa aaa gag agg gct tac aac agg tagtttgtgg acaggcgcct<br>Lys Ser Lys Lys Glu Arg Ala Tyr Asn Arg<br>285　　　　　　　　290 | 917 |
| ggtgtgagga ggacaaaata aaccgtgtat ttattacatt gctgcctttg ttgaggtgca | 977 |
| aggagtgtaa aatgtatatt tttaaagaat gttagaaaag gaaccattcc tttcataggg | 1037 |
| atggcagtga ttctgtttgc cttttgtttt cattggtaca cgtgtaacaa gaaagtggtc | 1097 |
| tgtggatcag cattttagaa actacaaata taggtttgat tcaacactta agtctcagac | 1157 |
| tgatttcttg cgggaggagg gggactaaac tcaccctacc acattaattg tggaaggaaa | 1217 |
| atatttcatt agctttttta ttttaataca agtaatatta ttactttatg aacaattttt | 1277 |
| tttaattggc catgtcgcca aaaatacagc ctatagtaaa tgtgtttctt gctgccatga | 1337 |
| tgtatatcca tataacaatt cagtaacaaa ggtttaaagt ttgaagatta ttttttaaaa | 1397 |
| aggtaaaagg ttaaatttta catgacagat attttatcta ttggcctgtt ccccaaatgg | 1457 |
| ccattttaaa atgcttgggt acacttctct taagtggtct agtcaaggaa cctcaagtca | 1517 |
| tgcttttgct atcaccaatc atagtgtacc catctttaat ttatatcagg tgtataaatg | 1577 |
| tacatttcca aatgaacttg cactgtaata ttataattgg aagtgcagtc agcagtagct | 1637 |
| gtcggagcta atgtcacaat tatgtgcaaa ggtgtgcttc ctgctgtatg tgagctgtaa | 1697 |
| aaatgttacg tgaagaaata aatgaaactt ggccagtttg ttcctctagt agtatattta | 1757 |
| attttgacat aagtaacttt taaaatttgt cttaaaaatt tatacaccag caatttagac | 1817 |
| aaagccttaa gcaaattttg tattattgtt ctcacttatt attaataatg aagtagaagt | 1877 |
| tacttaattg ccagcaaata aatacgtgtc aaaaagaat ctgtattcag acccctgggg | 1937 |
| tcaggaaatt actgccccac ttgtcaagtt cagcccacca tctgtttgaa cattatatga | 1997 |
| agtttaaatt ctagtgtcca taaataaagt ttcagggcca cccaaaaaaa aaaaaaaaa | 2057 |
| aaaa | 2061 |

<210> SEQ ID NO 2

```
<211> LENGTH: 294
<212> TYPE: PRT
<213> ORGANISM: Human

<400> SEQUENCE: 2

Met Pro Leu Cys Thr Ala Thr Arg Ile Pro Arg Tyr Ser Ser Ser Ser
  1               5                  10                  15

Asp Pro Gly Pro Val Ala Arg Gly Arg Gly Cys Ser Ser Asp Arg Leu
             20                  25                  30

Pro Arg Pro Ala Gly Pro Ala Arg Arg Gln Phe Gln Ala Ala Ser Leu
         35                  40                  45

Leu Thr Arg Gly Trp Gly Arg Ala Trp Pro Trp Lys Gln Ile Leu Lys
     50                  55                  60

Glu Leu Asp Glu Cys Tyr Glu Arg Phe Ser Arg Glu Thr Asp Gly Ala
 65                  70                  75                  80

Gln Lys Arg Arg Met Leu His Cys Val Gln Arg Ala Leu Ile Arg Ser
                 85                  90                  95

Gln Glu Leu Gly Asp Glu Lys Ile Gln Ile Val Ser Gln Met Val Glu
            100                 105                 110

Leu Val Glu Asn Arg Thr Arg Gln Val Asp Ser His Val Glu Leu Phe
        115                 120                 125

Glu Ala Gln Gln Glu Leu Gly Asp Thr Val Gly Asn Ser Gly Lys Val
    130                 135                 140

Gly Ala Asp Arg Pro Asn Gly Asp Ala Val Ala Gln Ser Asp Lys Pro
145                 150                 155                 160

Asn Ser Lys Arg Ser Arg Arg Gln Arg Asn Asn Glu Asn Arg Glu Asn
                165                 170                 175

Ala Ser Ser Asn His Asp His Asp Asp Gly Ala Ser Gly Thr Pro Lys
            180                 185                 190

Glu Lys Lys Ala Lys Thr Ser Lys Lys Lys Arg Ser Lys Ala Lys
        195                 200                 205

Ala Glu Arg Glu Ala Ser Pro Ala Asp Leu Pro Ile Asp Pro Asn Glu
    210                 215                 220

Pro Thr Tyr Cys Leu Cys Asn Gln Val Ser Tyr Gly Glu Met Ile Gly
225                 230                 235                 240

Cys Asp Asn Asp Glu Cys Pro Ile Glu Trp Phe His Phe Ser Cys Val
                245                 250                 255

Gly Leu Asn His Lys Pro Lys Gly Lys Trp Tyr Cys Pro Lys Cys Arg
            260                 265                 270

Gly Glu Asn Glu Lys Thr Met Asp Lys Ala Leu Glu Lys Ser Lys Lys
        275                 280                 285

Glu Arg Ala Tyr Asn Arg
    290

<210> SEQ ID NO 3
<211> LENGTH: 20
<212> TYPE: DNA
<213> ORGANISM: Human

<400> SEQUENCE: 3
gaagcggcgg atgctgcact                                              20

<210> SEQ ID NO 4
<211> LENGTH: 20
<212> TYPE: DNA
<213> ORGANISM: Human
```

-continued

<400> SEQUENCE: 4
acgcacgaga agtggaacca                                              20

<210> SEQ ID NO 5
<211> LENGTH: 24
<212> TYPE: DNA
<213> ORGANISM: Human

<400> SEQUENCE: 5
cggagtcaac ggatttggtc gtat                                         24

<210> SEQ ID NO 6
<211> LENGTH: 24
<212> TYPE: DNA
<213> ORGANISM: Human

<400> SEQUENCE: 6
agccttctcc atggtggtga agac                                         24

<210> SEQ ID NO 7
<211> LENGTH: 20
<212> TYPE: DNA
<213> ORGANISM: Human

<400> SEQUENCE: 7
ctgaaggagc tagacgagtg                                              20

<210> SEQ ID NO 8
<211> LENGTH: 20
<212> TYPE: DNA
<213> ORGANISM: Human

<400> SEQUENCE: 8
ggcttgtcag actgcgctac                                              20

<210> SEQ ID NO 9
<211> LENGTH: 20
<212> TYPE: DNA
<213> ORGANISM: Human

<400> SEQUENCE: 9
gacaacgacg agtgccccat                                              20

<210> SEQ ID NO 10
<211> LENGTH: 22
<212> TYPE: DNA
<213> ORGANISM: Human

<400> SEQUENCE: 10
ctacctgttg taagccctct ct                                           22

<210> SEQ ID NO 11
<211> LENGTH: 269
<212> TYPE: PRT
<213> ORGANISM: Human

<400> SEQUENCE: 11

Met Leu Ser Pro Ala Asn Gly Glu Gln Leu His Leu Val Asn Tyr Val
 1               5                  10                  15

Glu Asp Tyr Leu Asp Ser Ile Glu Ser Leu Pro Phe Asp Leu Gln Arg
                20                  25                  30

Asn Val Ser Leu Met Arg Glu Ile Asp Ala Lys Tyr Gln Glu Ile Leu

```
                35                  40                  45
Lys Glu Leu Asp Glu Cys Tyr Glu Arg Phe Ser Arg Glu Thr Asp Gly
     50                  55                  60

Ala Gln Lys Arg Arg Met Leu His Cys Val Gln Arg Ala Leu Ile Arg
 65                  70                  75                  80

Ser Gln Glu Leu Gln Asp Glu Lys Ile Gln Ile Val Ser Gln Met Val
                 85                  90                  95

Glu Leu Val Glu Asn Arg Thr Arg Gln Val Asp Ser His Val Glu Leu
            100                 105                 110

Phe Glu Ala Gln Gln Glu Leu Gly Asp Thr Val Gly Asn Ser Gly Lys
        115                 120                 125

Val Gly Ala Asp Arg Pro Asn Gly Asp Ala Val Ala Gln Ser Asp Lys
130                 135                 140

Pro Asn Ser Lys Arg Ser Arg Gln Arg Asn Asn Glu Asn Arg Glu
145                 150                 155                 160

Asn Ala Ser Ser Asn His Asp His Asp Gly Ala Ser Gly Thr Pro
                165                 170                 175

Lys Glu Lys Lys Ala Lys Thr Ser Lys Lys Lys Arg Ser Lys Ala
            180                 185                 190

Lys Ala Glu Arg Glu Ala Ser Pro Ala Asp Leu Pro Ile Asp Pro Asn
        195                 200                 205

Glu Pro Thr Tyr Cys Leu Cys Asn Gln Val Ser Tyr Gly Glu Met Ile
    210                 215                 220

Gly Cys Asp Asn Asp Glu Cys Pro Ile Glu Trp Phe His Phe Ser Cys
225                 230                 235                 240

Val Gly Leu Asn His Lys Pro Lys Gly Lys Trp Tyr Cys Pro Lys Cys
                245                 250                 255

Arg Gly Glu Asn Glu Lys Thr Met Asp Lys Ala Leu Glu
            260                 265

<210> SEQ ID NO 12
<211> LENGTH: 182
<212> TYPE: DNA
<213> ORGANISM: Human

<400> SEQUENCE: 12
ttgtagtttc taaaatgctg atccacagac cactttcttg ttacacgtgt accaatgaaa      60
acaaaaggca acagaatca ctgccatccc tatgaaagga atggttcctt ttctaacatt     120
ctttaaaaat atacatttta cactccttgc acctcaacaa aggcagcaat gtaataaata    180
ca                                                                    182

<210> SEQ ID NO 13
<211> LENGTH: 210
<212> TYPE: PRT
<213> ORGANISM: Human

<400> SEQUENCE: 13

Met Leu His Cys Val Gln Arg Ala Leu Ile Arg Ser Gln Glu Leu Gln
  1               5                  10                  15

Asp Glu Lys Ile Gln Ile Val Ser Gln Met Val Glu Leu Val Glu Asn
             20                  25                  30

Arg Thr Arg Gln Val Asp Ser His Val Glu Leu Phe Glu Ala Gln Gln
         35                  40                  45

Glu Leu Gly Asp Thr Val Gly Asn Ser Gly Lys Val Gly Ala Asp Arg
     50                  55                  60
```

```
Pro Asn Gly Asp Ala Val Ala Gln Ser Asp Lys Pro Asn Ser Lys Arg
 65                  70                  75                  80

Ser Arg Arg Gln Arg Asn Asn Glu Asn Arg Glu Asn Ala Ser Ser Asn
             85                  90                  95

His Asp His Asp Asp Gly Ala Ser Gly Thr Pro Lys Glu Lys Lys Ala
            100                 105                 110

Lys Thr Ser Lys Lys Lys Arg Ser Lys Ala Lys Ala Glu Arg Glu
        115                 120                 125

Ala Ser Pro Ala Asp Leu Pro Ile Asp Pro Asn Glu Pro Thr Tyr Cys
        130                 135                 140

Leu Cys Asn Gln Val Ser Tyr Gly Glu Met Ile Gly Cys Asp Asn Asp
145                 150                 155                 160

Glu Cys Pro Ile Glu Trp Phe His Phe Ser Cys Val Gly Leu Asn His
                165                 170                 175

Lys Pro Lys Gly Lys Trp Tyr Cys Pro Lys Cys Arg Gly Glu Asn Glu
            180                 185                 190

Lys Thr Met Asp Lys Ala Leu Glu Lys Ser Lys Lys Glu Arg Ala Tyr
        195                 200                 205

Asn Arg
    210
```